US007318917B2

(12) United States Patent
Schwartz et al.

(10) Patent No.: US 7,318,917 B2
(45) Date of Patent: Jan. 15, 2008

(54) RAPID ASSAYS FOR NEUROTRANSMITTER TRANSPORTERS

(75) Inventors: Joel W. Schwartz, Nashville, TN (US); Randy D. Blakely, Brentwood, TN (US); Louis DeFelice, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 546 days.

(21) Appl. No.: 10/656,897

(22) Filed: Sep. 5, 2003

(65) Prior Publication Data

US 2004/0115703 A1 Jun. 17, 2004

Related U.S. Application Data

(60) Provisional application No. 60/408,839, filed on Sep. 6, 2002.

(51) Int. Cl.
*A61K 49/00* (2006.01)
*A61K 38/43* (2006.01)
*C07D 487/00* (2006.01)
*C12N 9/00* (2006.01)
*C07K 14/01* (2006.01)

(52) U.S. Cl. .......................... 424/9.2; 532/1; 435/183; 424/94.1; 530/350

(58) Field of Classification Search ...................... None
See application file for complete search history.

(56) References Cited

U.S. PATENT DOCUMENTS

| 5,312,734 | A | 5/1994 | Uhl et al. ................... 435/69.1 |
| 5,418,162 | A | 5/1995 | Blakely et al. ........... 435/252.3 |
| 5,424,185 | A | 6/1995 | Lam et al. ....................... 435/6 |
| 6,127,133 | A | 10/2000 | Akong et al. ................ 435/7.2 |

OTHER PUBLICATIONS

Schwartz et al., 2003, J. Biol. Chem. 278 (11): 9768-9777.*
Brandis, K., 2006, Eukaryon, 2: 22-27.*
Peter, et al, 1996, J. Biol. Chem., 271(6): 2979-2986.*
Mason, et al, 2005, J. Neurosci. Methods, 143: 3-25.*
Schwartz, et al, 2003, J. Biol. Chem., 278(11): 9768-9777.*
Apparsundaram et al., "Molecular cloning and characterization of an L-epinephrine transporter from sympathetic ganglia of the bullfrog, rana catesbiana," *J. Neurosci.*, 17(8):2691-2702, 1997.
Aston-Jones et al., "Role of locus coeruleus in attention and behavioral flexibility," *Biol. Psychiatry*, 46:1309-1320, 1999.
Axelrod and Kopin, "The uptake, storage, release and metabolism of noradernaline in sympathetic nerves," *Prog. Brain Res.*, 31:21-32, 1969.
Bannon, "The human dopamine transporter gene: gene organization, transcriptional regulation, and potential involvement in neuropsychiatric disorders," *Eur. Neuropsychopharmacol.*, 11(6):449-455, 2001.
Barker and Blakely, "Identification of a single amino acid, phenylalanine 586, that is responsible for high affinity interactions of tricyclic antidepressants with the human serotonin transporter," *Mol. Pharmacol.*, 50(4):957-965, 1996.
Barnes, "Breaking the cycle of addiction," *Science*, 241:1029-1030, 1988.
Beiderman and Spencer, "Attention-deficit/hyperactivity disorder(ADHD) as a noradrenergic disorder," *Biol. Psychiatry*, 46:1234-1242, 1999.
Blakely and Apparsundaram, "Structural diversity in the catecholamine transporter gene family: molecular cloning and characterization of an L-epinephrine transporter from bullfrog sympathetic ganglia," *Adv. Pharmacol*, 42:206-210, 1998.
Blakely et al., "Cloning and expression of a functional serotonin transporter from rat brain," *Nature*, 354:66-70, 1991.
Blundell, "Serotonin manipulations and the structure of feeding behaviour," *Appetite*, 7(1):39-56, 1986.
Bönisch and Harder, "Binding of 3H-desipramine to the neuronal noraderenaline carrier of rat phaeochromocytoma cells (PC-12 cells)," *Naunym Schmeidebergs Arch. Pharmacol.*, 334:403-411, 1986.
Bönisch, "The transport of (+)-amphetamine by the neuronal noradrenaline carrier," *Naunyn Schmeidebergs Arch. Pharmacol.*, 327:267-272, 1984.
Bruns et al., "A fast activating presynaptic reuptake current during serotonergic transmission in identified neurons of hiduro," *Neuron*, 10:559-572, 1993.
Bruns, "Serotonin transport in cultured leech neurons," *Methods Enzymol.*, 296:593-607, 1998.
Clarkson et al., "Electrophysiological effects of high cocaine concentrations on intact canine heart: evidence for modulation by both heart rate and autonomic nervous system," *Circulation*, 87:950-962, 1993.
Corey et al., "A cocaine-sensitive drosophila serotonin transporter: cloning, expression, and electrophsiological characterization," *Proc. Natl. Acad. Sci., USA*, 91:1188-1192, 1994.
Coull et al., "Noradrenergically mediated plasticity in a human attentional neuronal network," *Neuroimage*, 10:705-715, 1999.
DeFelice, "Visualization of single cell real-time kinetics for norepinephrine transporters using fluorescence microscopy," manuscript. In Prep. 2003.
DeFelice and Galli, "Electrophysiological analysis of transporter function," *Adv. Pharmacol.*, 42:186-190, 1998.
DeOliveara et al., "Differences in the temperature dependence of drug interaction with the noradrenaline and serotonin transporters," *Neuropharmacology*, 28(8):823-828, 1989.

(Continued)

*Primary Examiner*—Eileen B. O'Hara
*Assistant Examiner*—Sandra Wegert
(74) *Attorney, Agent, or Firm*—Fulbright & Jaworski L.L.P.

(57) ABSTRACT

The invention describes the finding that 4-(4-dimethylaminostyryl)-N-methylpyridinium or ASP$^+$ is a fluorescent substrate that is transported by several neurotransmitter transporters. Provided are methods for the analysis of neurotransmitter transport and binding using ASP$^+$. The invention also provides rapid methods for screening for modulators of neurotransmitter transport. As neurotransmitter transporter defects are associated with numerous neurological disorders, the invention also provides methods for treating neurotransmitter transport-associated defects/conditions using the modulators identified by the screening methods of the invention.

21 Claims, 12 Drawing Sheets

OTHER PUBLICATIONS

Dow and Kline, "Antidepressant treatment of posttramatic stress disorder and major depression in veterans," *Ann. Clin. Psychiatry,* 9(1):1-5, 1997.

Fleckenstein et al., "Differential effects of psychostimulants and related agents on dopaminergic and serotonergic transporter function," *Eur. J. Pharmacol.,* 382:45-49, 1999.

Gainetdinov et al., "Dopamine transporter is required for in vivo MPTP neurotoxicity: evidence from mice lacking the transporter," *J. Neurochem.,* 69:1322-1325, 1997.

Galli et al., "Norepinephrine transporters have channel modes of conduction," *PNAS,* 93:8671-8676, 1998.

Galli et al., "Sodium-dependent norepinephrine-induced currents in norepinephrine-transporter-transfected HEK-293 cells blocked by cocaine and antidepressants," *J. Exp. Biol.,* 198(10):2197-2212, 1995.

Gill et al., "Effects of serotonin uptake blockade on food, water, and ethanol consumption in rats," *Alcoholism,* 11(5):444-449, 1987.

Giros et al., "Cloning, pharmacological characterization, and chromosome assignment of the human dopamine transporter," *Mol. Pharmacol.,* 42(3):383-390, 1992.

Giros et al., "Hyperlocation and indifference to cocaine and amphetamine in mice lacking the dopamine transporter," *Nature,* 379(6566):606-612, 1996.

Glassman et al., "Idiosyncratic pharmacokinetics complicating treatment of major depression in an elderly woman," *J. Nerv. Ment. Dis.,* 173(9):573-576, 1985.

Hadrich et al., "Synthesis and characterization of fluorescent ligands for the norepinephrine transporter: potential neuroblastoma imaging agents," *J. Med. Chem.,* 42:3101-3108, 1999.

Hartzell, "Distribution of muscarininc acetylcholine receptors and presynaptic nerve terminals in amphibian heart," *J. Cell Biol.,* 86:6-20, 1980.

Hatfield and McGaugh, "Norepinephrine infused into the basolateral amygdala posttraining enhancing retention in a spatial water maze task," *Neurobiol. Learn. Mem.,* 71:232-239, 1999.

Herrara and Banner, "The use and effects of vital fluorescent dyes: observation of motor nerve terminals and satellite cells in living frog muscles," *J. Neurocytol.,* 19:67-83, 1990.

Herrera et al., "Repeated, in vivo observation of frog neuromuscular junctions: remodeling involves concurrent growth and retraction," *J. Neurocytol.,* 19:85-99, 1990.

Hohage et al., "Regulation of organic cation transport in IHKE-1 and LLC-PK1 cells. Fluorometric studies with 4-(4-Dimethylaminostyryl)-N-methylpyridinium," *J. Phamacol. Exp. Ther.,* 286(1):305-310, 1998.

Iverson et al., "Uptake, storage, and metabolism of norepinephrine in tissues of the developing rat," *J. Pharmacol. Exp. Ther.,* 157(3):509-516, 1967.

Jacob et al., "Abnormal norepinephrine clearance and adrenergic receptor sensitivity in idiopathic orthostatic intolerance," *Circulation,* 99:1706-1712, 1999.

Jones, "Descending noradrenergic influences on pain," *Prog. Brain Res.,* 88:381-394, 1991.

Kawarai et al., "Structure and organization of the gene encoding human dopamine transporter," *Gene,* Aug. 11;195(1):11-8, 1997.

Kitayama et al., "Functional characterization of the splicing variants of human norepinephrine transporter," *Neurosci. Lett.,* 312(2):108-112, 2001.

Koella, "Serotonin and sleep," In: *Neuronal Seratonin,* Osborne et al. (eds.) 153-170, 1988.

Kuhar et al., "The dopamine hypothesis of the reinforcing properties of cocaine," *Trends Neurosci.,* 14(7):299-302, 1991.

Le Bars, "Serotonin and pain," In: *Neuronal Serotinin,* Osborne and Hamin (eds.), 171-229, 1988.

Masson et al., "Neurotransmitter transporters in the central nervous system," *Pharmacol. Rev.,* 51(3):439-464, 1999.

Mehrens et al., "The affinity of the organic cation transporter rOCT1 is increased by protein kinase C-dependant phosphorylation," *J. Am. Soc. Nephrol.,* 11:1216-1224, 2000.

Morozova et al., "[4-(n-Dimethylaminostryryl)-1-methylpyridinium fluorescence in a living cell]," *Tsitologiia,* 23(8):916-923, 1981.

Naranjo et al., "The serotinin uptake inhibitor citalophram attenuates ethanol intake," *Clin. Pharmacol. Ther.,* 41:266-274, 1987.

Nuemeister et al., "Association between serotonin transporter gene promoter polymorphism (5HTTLPR) and behavioral responses to tryptophan depletion in healthy women with and without family history of depression," *Arch. Gen. Psychiatry,* 59(7):613-620, 2002.

Pacholczyk et al., "Expression cloning of a cocaine-and antidepressant-sensitive human noradrenaline transporter," *Nature,* Mar. 28; 350(6316):350-354, 1991.

Pelham, "Green light for Golgi traffic," *Nature,* 389(6646):17, 19, 1997.

Pietruck and Ullrich, "Transport interactions of different organic cations during their excretion by the intact rat kidney," *Kidney Int.,* 47(6):1647-1657, 1995.

Porzgen et al., "Errata," *Biochem. Biophys. Res. Commuin.,* 227(2):642:643, 1996.

Prasad and Amara, "The dopamine transporter in mesencephalic cultures is refractory to physiological changes in membrane voltage," *J. Neurosci.,* 21(19):7561-7567, 2001.

Qian et al., "Protein kinase C activation regulates human serotonin transporters in HEK-293 cells via altered cell surface expression," *The Journal of Neuroscience,* 17(1):45-57, 1997.

Ramamoorthy et al., "Antidepressant- and cocaine-sensitive human serotinin transporter: molecular cloning, expression, and chromosomal localization," *Proc. Natl. Acad. Sci., USA,* 90:2542-2546, 1993.

Ramamoorthy et al., "Expression of a cocaine-sensitive norepinephrine transporter in the human placental syncytiotrophoblast," *Biochemistry,* 32(5):1346-1353, 1993.

Ramamoorthy, "Phosphorylation and regulation of antidepressant-senstive serotonin transporters," *J. Biol. Chem.,* 273(4):2458-2466, 1998.

Ressler and Nemeroff, "Role of norepinephrine in the pathophysiology and treatment of mood disorders," *Biol. Psychiatry,* 46:1219-1233, 1999.

Rohlicek and Ullrich, "Simple device for continuous measurement of fluorescent anions and cations in the rat kidney in situ," *Ren. Physiol. Biochem.,* 17(2):57-61, 1994.

Rudnick and Clark, "From synapse to vesicle: the reuptake and storage of biogenic amine neurotransmitters," *Biochim. Biophys. Acta,* 1144(3):249-263, 1993.

Samochowiec et al., "Polymorphisms in the dopmaine, serotonin, and norepinephrine transporter genes and their relationship to temperament and character inventory in healthy volunteers," *Neuropsychobiology,* 43(4):248-253, 2001.

Schroeter et al., "Immunolocalization of the cocaine- and antidepressant-sensitive 1-norepinephrine transporter," *J. Comp. Neurol.,* 420(2):211-232, 2000.

Silverstone et al., "Serotoninergic mechanisms in human feeding: the pharmacological evidence," *Appetite,* 7 Suppl., 85-97, 1986.

Skrebitsky and Chepkova, "Hebbian synapses in cortical and hippocampal pathways," *Rev. Neurosci.,* 9:243-264, 1998.

Smith and Levi, "LLC-PK1 cells stably expressing the human norepinephrine transporter: a functional model of carrier-mediated norepinephrine release in protracted myocardial ischemia," *J. Pharmacol Exp. Ther.,* 291(2):456-463, 1999.

Soubrié, "Serotinin and behaviour, with special regard to animal models of anxiety, depression and waiting ability," In: *Neuronal Serotonin,* Osborne and Hamon (eds.), 255-270, 1988.

Southwick et al., "Role of norepinephrine in the pathophysiology and treatment of posttramatic stress disorder," *Biol. Psychiatry,* 46:1192-1204, 1999.

Stachon et al., "Characterisation of organic cation transport across the apical membrane of proximal tubular cells with the fluorescent dye 4-Di-1-ASP," *Cell Physiol. Biochem.,* 7:264-274, 1997.

Steffgen et al., "Dynamic monitoring of organic cation transport processes by flourescence measurements in LLC-PK1 cells," *Cellular Physiol. Biocem.,* 6:72-91, 1996.

Stöber et al., "Serotonin transporter gene polymorphism and affective disorder," *Lancet,* 347(9011):1340-1341, 1996.

Tsai et al., "Association for serotonin transporter gene variable number tandem repeat polymorphism and schizophrenic disorders," *Neuropsychobiology,* 45(3):131-133, 2002.

Van Woert et al., "Serotonin and myoclonus," *Monogr. Neural. Sci.,* 3:71-80, 1976.

Watanabe et al., "Cardiovascular effects of imipramine in intact dogs and isolated dog atria," *Jpn. Heart J.,* 22:977-985, 1981.

White, "Inhibition of synaptosomal noradrenaline uptake by veratridine, gramicidin D and valinomycin," *J. Neurochem.,* 29:193-198, 1977.

Wu et al., "Structural and functional characteristics and tissue distribution pattern of rat OCTN1, an organic cation transporter, cloned from placenta," *Biochim. Biophys. Acta.,* 1466:315-327, 2000.

\* cited by examiner

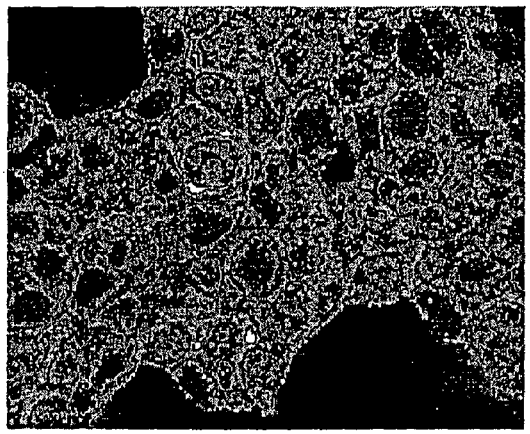
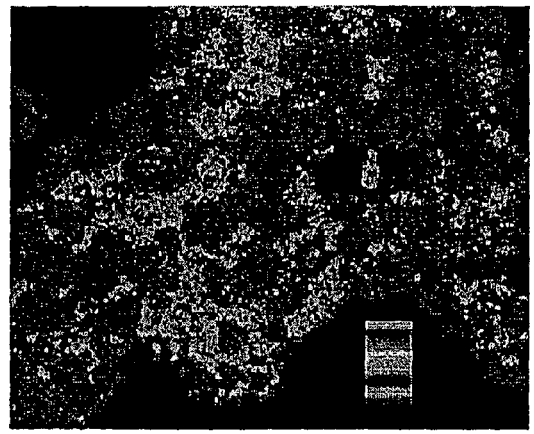
FIG. 6A
FIG. 6B
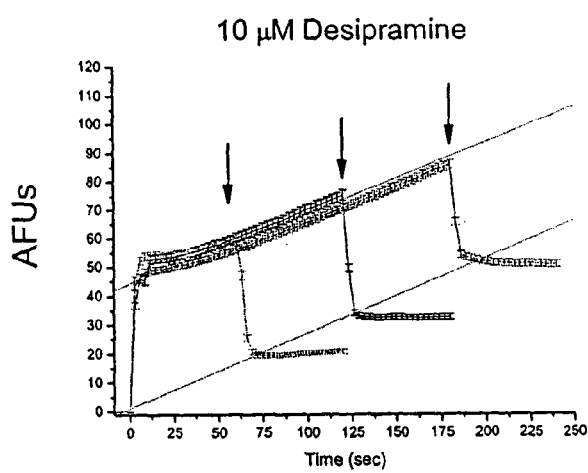
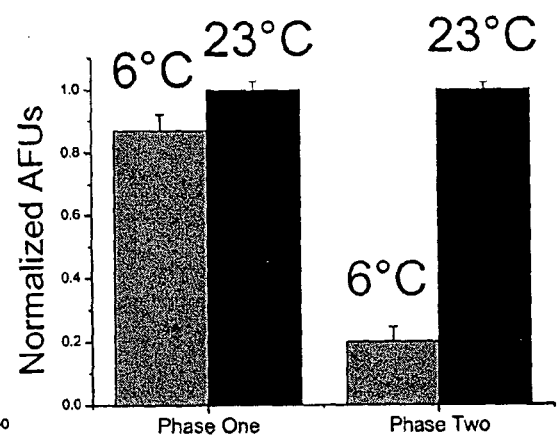
FIG. 6C
FIG. 6D

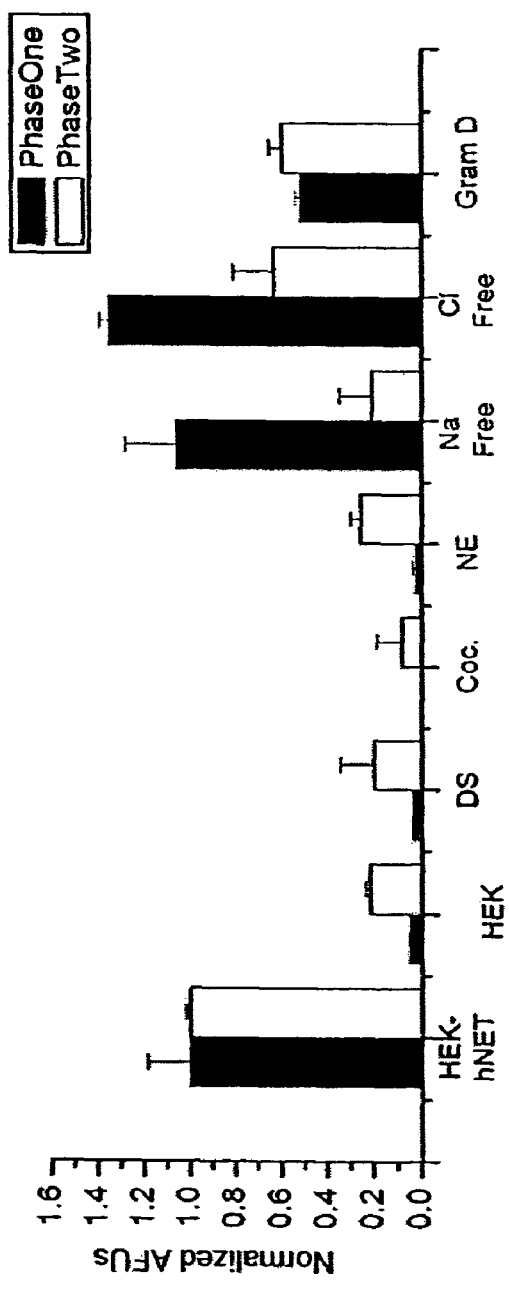
FIG. 7A
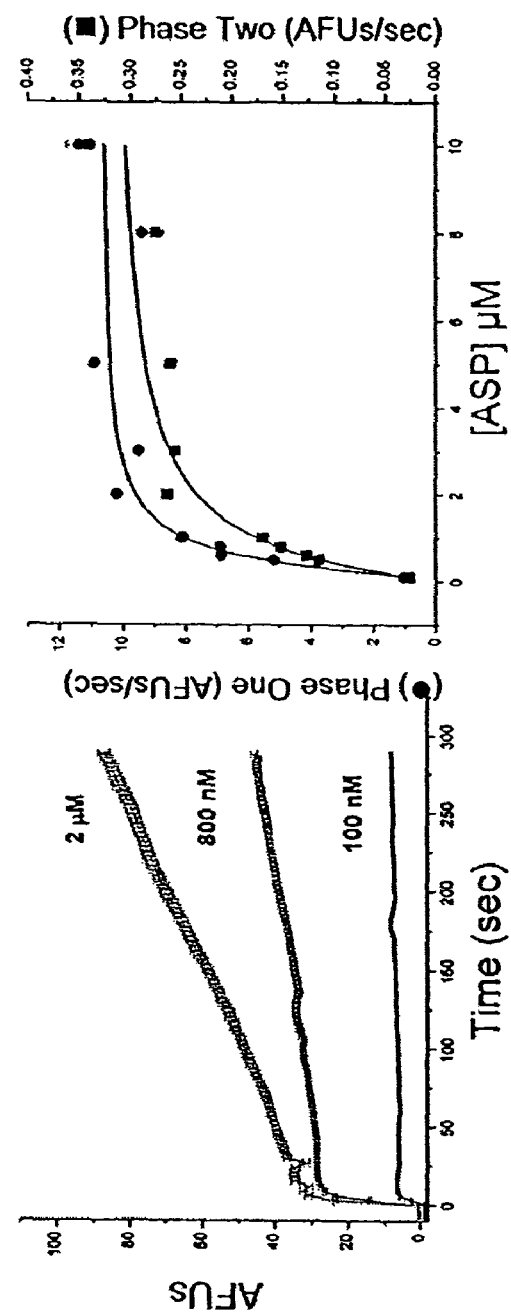
FIG. 7B
FIG. 7C

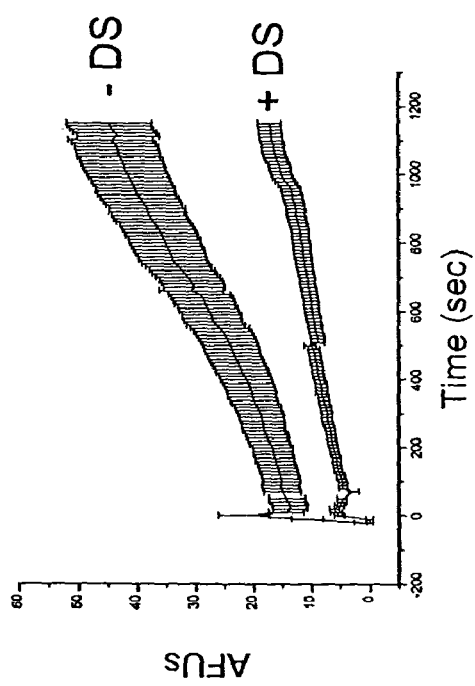
FIG. 8A
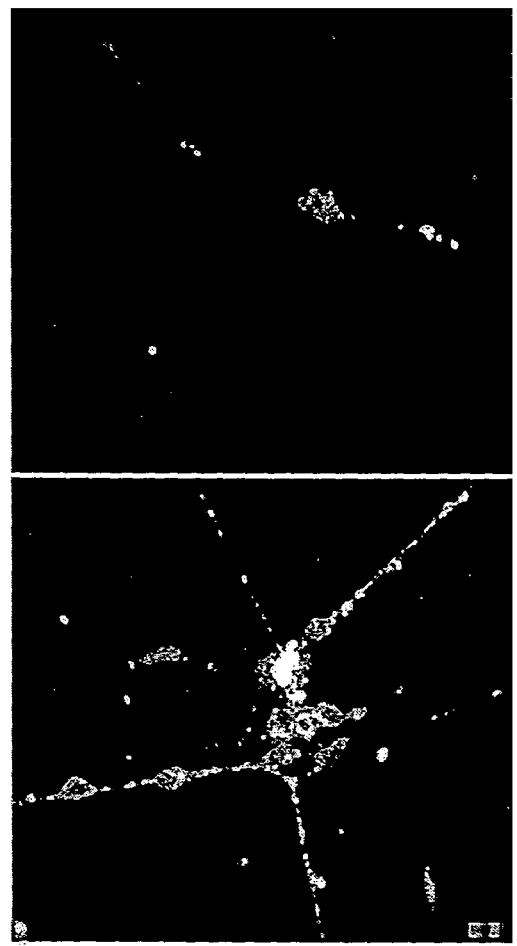
FIG. 8B
FIG. 8C

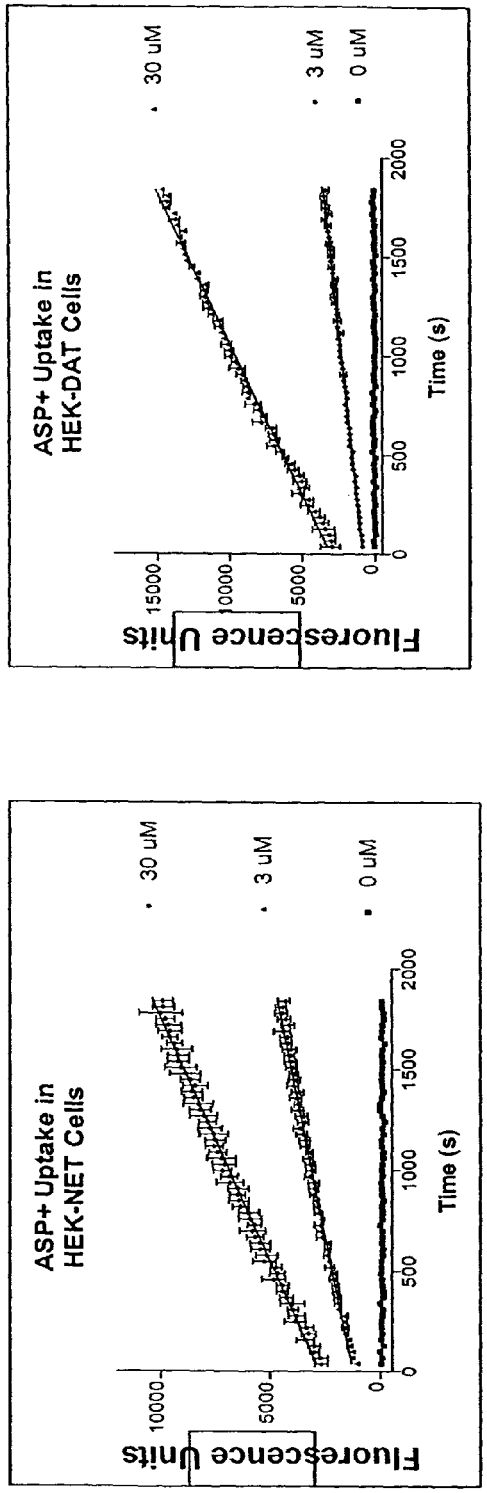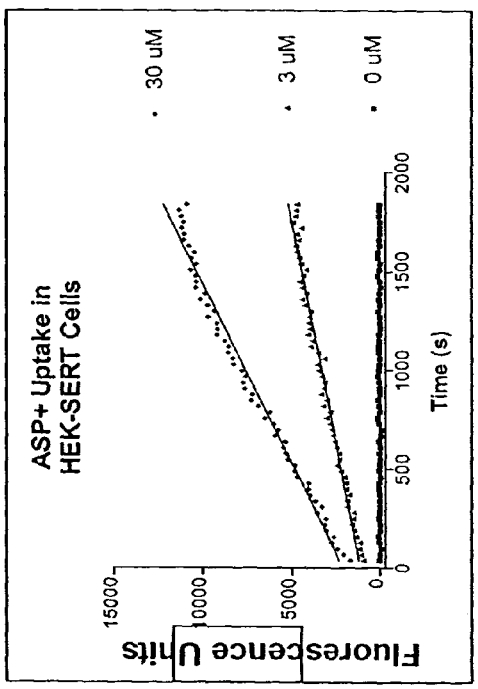
FIG. 10A
FIG. 10B
FIG. 10C

RAPID ASSAYS FOR NEUROTRANSMITTER TRANSPORTERS

The present application claims priority to now abandoned U.S. Provisional Patent Application Ser. No. 60/408,839 filed Sep. 6, 2002. The entire text of the above-referenced disclosure is specifically incorporated herein by reference without disclaimer. The government owns rights in the present invention pursuant to grant numbers NS-34075, NS-33373 and DA016338 from the National Institutes of Health.

BACKGROUND OF THE INVENTION

1. Field of the Invention

The present invention relates generally to the fields of neurobiology and neurophysiology. More particularly, it concerns the development of methods for measuring the transport and binding of neurotransmitter transporters using ASP$^+$ and other fluorescent substrates. The invention also provides screening methods for identifying modulators of neurotransmitter transport.

2. Description of Related Art

Neurotransmitters mediate signal transduction in the nervous system and modulate the processing of responses to a variety of sensory and physiological stimuli. An important regulatory step in neurotransmission is the inactivation of a neurotransmitter following its release into the synaptic cleft. This is especially true for the biogenic amine and amino acid neurotransmitters. Inactivation of a neurotransmitter is typically mediated by uptake of the released neurotransmitter by neurotransmitter transporters that are located on the presynaptic neuron or in some cases on adjacent glial cells. Thus, neurotransmitter transporters are central to the processing of information in the nervous system and are associated with numerous neurological disorders.

For example, the neurotransmitter norepinephrine (also called noradrenalin) transduces signaling in the central nervous system that modulates attention, mood, arousal, learning, and memory (Aston-Jones et al., 1999; Coull et al., 1999; Skrebitsky and Chepkova, 1998; Hatfield and McGaugh, 1999). Norepinephrine (NE) transporters (NETs) attenuate neuronal signaling via rapid neurotransmitter clearance (Ressler and Nemeroff, 1999; Iversen et al., 1967; Axelrod and Kopin, 1969; Blakely et al., 1991). Norepinephrine transport is implicated in the pathology of major depression, post-traumatic stress disorder and attention deficit disorder (Ressler and Nemeroff, 1999; Southwick et al., 1999; Dow and Kline, 1997; Biederman and Spencer, 1999). Therapeutic agents that inhibit NET can elevate the concentration of norepinephrine in the brain and periphery (Axelrod and Kopin, 1969; Bonisch, 1984; Ramamoorthy et al., 1993; Galli et al., 1995; Corey et al., 1994; Fleckenstein et al., 1999). Noradrenergic signaling in the peripheral nervous system influences blood pressure and heart rate (Jones, 1991; Jacob et al., 1999; Hartzell, 1980), and NET inhibitors, such as cocaine and antidepressants, induce cardiac complications (Watanabe et al., 1981; Clarkson et al., 1993; Glassman et al., 1985).

Similarly other neurotransmitters such as epinephrine (E), dopamine (DA), serotonin (SE), and their respective transporters such as epinephrine transporters (ET), dopamine transporters (DAT), and the serotonin transporters (SERT), mediate diverse aspects of neuronal signaling and are involved in the pathology of numerous nervous system related disorders. Thus, neurotransmitter transporters are the targets of various therapeutic agents used in the treatment of neurological disorders including, depression, epilepsy, schizophrenia, Parkinson's disease, attention deficit disorders, eating and sleeping disorders as well as some neurodegenerative disorders. In some instances, treatment of these disorders is mediated by the use of pharmaceutical agents that are antagonists of a neurotransmitter transporter. Antagonists block uptake and prolong and/or enhance the action of the neurotransmitter. In other instances, treatment is mediated by use of pharmaceutical agents that are agonists of a neurotransmitter transporter. Agonists enhance uptake and rapidly clear the neurotransmitter, thereby terminating its actions. For example, imipramine, a blocker of SE and NE uptake, is used as an antidepressants; benztropine, an antagonist of dopamine uptake, temporarily alleviates the symptoms of Parkinson's disease; and blockers of γ-amino butyric acid (GABA) uptake are used in the treatment of epilepsy.

Despite the relevance of neurotransmitter transporters, the art is hindered by very limited methods that are used in studying neurotransmitter transporter functions such as kinetics, affinity, temporal and spatial aspects of transport, voltage dependence and other transport mechanics (Galli et al., 1995; Corey et al., 1994; DeFelice & Galli, 1998; Prasad and Amara, 2001). Methods used to study neurotransmitter transport typically involve the use of radiometric substrates to measure neurotransmitter accumulation. For example, $^3$H-labeled neurotransmitters are typically used to study transport of serotonin, epinephrine, norepinephrine, dopamine and the amino-acid transmitters (see for example U.S. Pat. No. 5,424,185; Bonisch 1984; Bonisch and Harder, 1986; Hadrich et al., 1999). Although radiolabel techniques offer high specificity, these approaches have significant limitations such as poor time and spatial resolution. In addition, none of these methods have the intrinsic capability to distinguish substrate binding from transport in the same assay. For example, non-permeating radiolabeled molecules that bind neurotransporters can characterize binding and count transporters, and permeating radiolabeled molecules can characterize transport, however, because of the poor time resolution of radiometric assays, it is not possible to study binding and transport during the same experiment. Furthermore, these methods are not applicable for studying transport function in single mammalian cells. Although electrophysiology and amperometry alleviate some of these constraints, eletrophysiology although rapid (in the millisecond time resolution) has poor substrate selectivity, while amperometry has the reverse characteristics (DeFelice and Galli, 1998; Galli et al., 1998).

Several other studies involved the use of fluorescent analogs of neurotransmitters for the study of neurotransmitter transporters. For example, Hadrich and colleagues generated fluorescent NE and nisoxetine analogs to image neuroblastomas (Hadrich et al., 1999), and Bruns (1998) used a autofluorescent analog of serotonin (5-HT), 5,7-dihydrotryptamine to identify a serotonin uptake current in leech neurons, however, these fluorescent compounds were also unable to distinguish substrate binding from transport. Thus, new methods for the analysis of neurotransmitter transport finction are highly desirable.

In addition, the art also lacks cost effective and rapid screening methods to identify modulators of neurotransmitter transporters that may be useful as therapeutic agents in the treatment of nervous system disorders.

SUMMARY OF THE INVENTION

The present invention overcomes the defects in the art and provides methods for the analysis of neurotransmitter transporters based on the use of fluorescent substrates. The invention also provides screening methods to identify agents that can modulate neurotransmitter transporters.

In particular embodiments, the present invention provides that 4-(4-dimethylaminostyrl)-N-methylpyridinium (ASP$^+$) is transpoters by neurotransmitter transporters such as DAT, NET and SERT and can used for measuring neurotransmitter transport.

Thus, the present invention provides methods for measuring neurotransmitter transport in a cell or cellular extract comprising providing a cell that expresses a neurotransmitter transporter or a cellular extract that comprises a neurotransmitter transporter; exposing the cell or the extract to ASP$^+$; and measuring the transport of ASP$^+$; thereby measuring the transport of the neurotransmitter in the cell.

The term "neurotransmitter transporter" or "transporter" is used herein to describe a membrane protein which, under physiologic conditions, is at least substantially specific for the transport of at least one neurotransmitter.

The measurement of ASP$^+$ transport is performed by fluorescence microscopy. In other embodiments, one may measure transport by using a fluorescent plate reader. In some embodiments of the invention, measuring transport further comprises measuring the kinetics of the neurotransmitter transporter. In yet other embodiments, measuring transport is in real time. In some specific embodiments, the time resolution of measuring transport is 1 hour to 50 milliseconds. In yet other embodiments, one may measure the voltage dependence, the turnover rate, the surface expression, and/or binding constants of the transporter. In still other embodiments, measuring transport includes characterizing the kinetics, affinity, uptake of neurotransmitter, retention or accumulation of neurotransmitter or other substrate, regulation by phosphorylation or other biochemical modifications.

In some embodiments, measurement of transport characteristics is achieved in cells transfected to express the transporter. In other embodiments, the measurement of transport is in non-transfected neurons in tissue culture and allows the characterization of endogenous transport regulation and function.

In some embodiments, transport is measured in a single cell. In other embodiments, transport is measured in a single neuronal process. In yet other embodiments, transport is measured in more than one cell or in a population of cells. Transport may be measured simultaneously from numerous samples using multi-well formats, fluorescent plate readers, and other automated methods known in the art.

The neurotransmitter transporter maybe endogenously expressed by the cell. In alternative embodiments, the neurotransmitter transporter is expressed exogenously by the cell. Recombinant DNA technology may be used to express any neurotransmitter transporter exogenously in a cell using methods of molecular biology as are known to one of skill in the art. The specification provides detailed description of methods used for exogenous expression infra. One of skill in the art would be well equipped to construct an expression vector that expresses nucleic acids encoding any neurotransmitter transporter using standard molecular biology techniques (see, for example, Maniatis et al., 1988 and Ausubel et al., 1994, both incorporated herein by reference). Furthermore, Galli et al. (1995), Ramamoorthy (1998), and U.S. Pat. Nos. 5,312,734, 5,418,162, & 5,424,185, all incorporated herein by reference, describe numerous nucleic acids, constructs and host cells used to express neurotransmitter transporters.

In specific embodiments, the neurotransmitter transporter is a monoamine neurotransmitter transporter and may be a norepinephrine transporter, an epinephrine transporter, a dopamine transporter, or a serotonin transporter. It is also contemplated that the methods of the present invention will be applicable to other neurotransmitter transporters including GABA transporters, glutamate transporters, and glycine transporters, provided the fluorescent substrate that is used is transported by these transporters.

In other specific embodiments, the cell is a neuronal cell. In yet other specific embodiments, the cell expressing the neurotransmitter transporter may be a blood platelet, a placental cell or a trophoblast.

In embodiments where cellular extracts comprising one or more neurotransmitter transporter are used, the cellular extracts may further comprise cell membranes. The term "cellular extract" is defined herein as a complex biochemical and aqueous solution comprising one or more neurotransmitter transporter(s). It is contemplated that the cellular extract may also comprise endogenous regulators and modulators of neurotransmitters. Typically, the neurotransmitter will be comprised in a cell membrane. Cells expressing neurotransmitter transporters may be lysed to provide cell membranes and/or cellular extracts. The cellular extract may be from any cell that endogenously expresses a neurotransmitter transporter, such as a neuronal cell, a blood platelet, a placental cell, a trophoblast or may be from any cell that is engineered to exogenously express a neurotransmitter transporter. In some specific embodiments, the cell membranes may be from cells that are engineered to exogenously express a single type of neurotransmitter transporter and therefore is free of other neurotransmitter transporters. This allows the analysis of only one type of neurotransmitter transporter in isolation. One may also analyze the effects of other molecules or interacting proteins on the neurotransmitter transporter.

In other embodiments, it is contemplated that one may use analogs of ASP$^+$ such as, 4-(4-diethylaminostyrl)-N-methylpyridinium iodide (4-Di-2-ASP$^+$), 4-(4-dimethylaminostyrl)-N-methylpyridinium iodide (4-Di-1-ASP$^+$), 2-(4-dimethylaminostyrl)-N-methylpyridinium iodide (DASPMI), 2-(4-dimethylaminostyrl)-N-ethylpyridinium iodide (DASPEI), and other members of the styryl pyridinium family of dyes (Herrera and Banner, 1990). It is also contemplated that one may also use dyes such as 3, 3'diethyloxadicarbocyanine iodide (DIOC) or acridine orange-10-nonyl bromide (NAO) (Herrera and Banner, 1990).

The invention also provides methods of screening for agents that can modulate the activity of a neurotransmitter transporter comprising providing a cell or cellular extract that expresses a neurotransmitter transporter; exposing the cell or cellular extract to an agent that is a candidate neurotransmitter transporter modulator; exposing the cell or cellular extract to ASP$^+$; measuring the transport of ASP$^+$; and comparing the transport of ASP$^+$ in the cell or cellular extract to the transport of ASP$^+$ in a cell or cellular extract that has not been exposed to the agent, thereby determining if the agent is a modulator of activity of the neurotransmitter transporter.

It is contemplated that the screening methods will be automated to provide high-throughput screening of agents. For example, in some embodiments, the methods comprise the simultaneous screening of multiple agents with potential neurotransmitter transporter modulatory activities. This may be achieved by addition of reagents/components of the assay using robotic fluid delivery (see Example 3 and FIG. 9, FIG. 10 and FIG. 11 for the use of FLEXstation (Molecular Devices)); the analysis of multiple samples in multi-well formats; using a fluorescent plate reader (also see Example 3 for examples of multiwell assays, plate readers and computerized software for data analysis) as well as other automation methods known in the art. Other examples of methods of automated equipment and assay procedures for membrane associated proteins such as ion channels are described in U.S. Pat. Nos. 6,127,133 and 5,670,113, the contents of which are incorporated by reference herein.

The screening methods of the invention may be in vitro or in cyto screening methods that use cells, cell lines, recombinant cells or cellular extracts thereof. Any cells which express a neurotransmitter transporter may be used in the screening methods, either as whole cells or lysed to provide cell membranes or cell extracts as described above.

The screening methods may also be performed using in vivo methods, for example using animal models. In some cases, the animals may be transgenic animals. It is contemplated that one may use animals such as mice or C. elegans as the genetics of these systems as well as methods for establishing transgenics are well known in these animals. Animals expressing certain types of neurotransmitter transporters can be provided with candidate modulatory agents and the transport of $ASP^+$ or other fluorescent substrate can be imaged in vivo or in situ. General methods for in vivo imaging using $ASP^+$ are described in Herrera and Banner (1990), and in Herrera et al. (1990), the contents of both are incorporated herein by reference. In situ methods for analysis of $ASP^+$ are exemplified by the work by Ullrich and colleagues (Pietruck and Ullrich, 1995; Rohlicek and Ullrich, 1994; the contents of both are incorporated herein by reference). These methods may be suitably modified with the other teachings of the specification. The present invention contemplates the use of these methods in conjunction with the screening methods described herein.

In some embodiments, measuring the transport of $ASP^+$ further comprises adding a quencher and measuring the polarization of light in the presence and absence of the modulatory agent. Quenchers allow reduction of unwanted background signals from the solution and also test the depth of ASP penetration in the membrane-bound transporter. Polarized light measures the mobility of the ASP molecules in solution as well as ASP molecules bound to the transporter, thus reporting the extent and location of binding.

Thus, the methods of the invention provide rapid assays for screening agents and are expected to provide therapeutic agents that are potentially useful for the treatment of disorders associated with neurotransmitter transporter function. By measuring and comparing changes in transport of $ASP^+$ (or other fluorescent substrate), in the presence and absence of the investigatory or candidate agent, one can further evaluate the role of the compound. For example, where an agent causes a change in a specific finction or transport mechanism, the agents may be further screened to determine the specific extent to which the compound acts as either an agonist or antagonist. It is also contemplated that the modulators may not be antagonists or agonists per say and may mediate their function by other mechanisms.

Agents that may be screened include substances or compounds that are naturally occurring such as, plant products or extracts and animal derived products, including macromolecular entities such as polypeptides, polynucleotides, lipids, sugars, small entities such as ligands, neurotransmitters, amino acids, elemental compounds as well as other organic compounds and inorganic compounds. The candidate agents may also be man-made substances such as synthetic compounds or pharmaceutical formulations of natural or synthetic agents. The synthetic compounds and/or natural products also include substances that are either part of a crude mixture or are partially to completely purified/isolated.

The invention also provides methods for the treatment of a nervous system disorder comprising administering to a patient in need thereof a neurotransmitter transporter modulator identified by the screening methods described above. These methods are contemplated to be useful in treatment of nervous system disorders such as, depression, hypertension, drug abuse and addiction, attention deficit disorder, neurodegeneration and others. It is envisioned that the therapeutic agents identified herein may be administered with other standard therapies that are normally used to treat the disorder or condition. In some embodiments of this facet, the modulatory agent maybe administered simultaneously, prior to or after the administration of the other drug or therapy that is routinely used to treat the disorder.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIG. 5C, hNET-HEK cells are exposed to 2 mM ASP+ under blue polarized light and red images were collected at 0° and 90° with respect to the incident polarization. Polarized images from ASP+ in solution, in the cytosol, and at the cell surface were collected from at least 40 cells in 4 dishes in FIG. 5D.

FIGS. 6A-6D. Desipramine displaces phase I ASP+ and arrests phase II transport. The top panels show confocal images of confluent HEK-hNET cells exposed to 2 mM ASP for 60 sec (FIG. 6A) followed by application of 10 mM desipramine (FIG. 6B). From similar data, FIG. 6C shows three separate HEK-hNET cells exposed to 2 mM ASP+ for 60, 120 or 180 seconds followed by rapid application of 10 mM desipramine. Data integrated over the entire cell were collected at 0.3 Hz to avoid photo-bleaching. The top line represents the slope of phase II and the bottom line the corresponding increase in sequestered ASP+ at each time (only three of six are shown). FIG. 6D shows the temperature dependence of phase I and phase II slopes in 2 mm ASP+. The slopes of phase I and II are normalized to room temperature. The color gradient in FIG. 6B represents ASP+ intensity.

FIGS. 7A-7C. ASP+ pharmacology. The bars in FIG. 7A correspond to normalized slopes of phase I and II under various treatments. Na+ and Cl− are replaced with NMDG+ and acetate, respectively. FIG. 7B shows the average pixel intensity from whole-cell confocal images as described in FIG. 3. External ASP+ is varied as indicated. FIG. 7C plots the kinetics of phase I and II as a function of ASP+ concentration. Values are represented at normalized slopes±STD of four experiments with 100 cells per experiment.

FIGS. 8A-8C. ASP+ accumulation in superior cervical ganglia (SCG) cells. FIG. 8A quantifies desipramine-sensitive accumulation by monitoring the increase in intracellular fluorescence within individual neurons. Comparing FIG. 8B (without desipramine (DS) and FIG. 8C (with DS) shows that ASP+ accumulation in superior cervical ganglia (SCG) cells is desipramine sensitive. The color gradient represented in FIG. 8A denotes the color range corresponding to the intensity values.

FIGS. 10A-10C. Concentration-response profiles for ASP+ accumulation in monoamine transporter transfected HEK-293 cells. Increasing concentrations of ASP+ were delivered to plated, adherent cells and the accumulation of ASP+ inside cells quantitated on the FLEXstation as described in Example 3. NET (FIG. 10A), DAT (FIG. 10B), and SERT (FIG. 10C), demonstrate concentration-dependent accumulation of ASP+ with accumulation well fit as a one site, nonsaturable transport process.

DESCRIPTION OF ILLUSTRATIVE EMBODIMENTS

Figure 1:
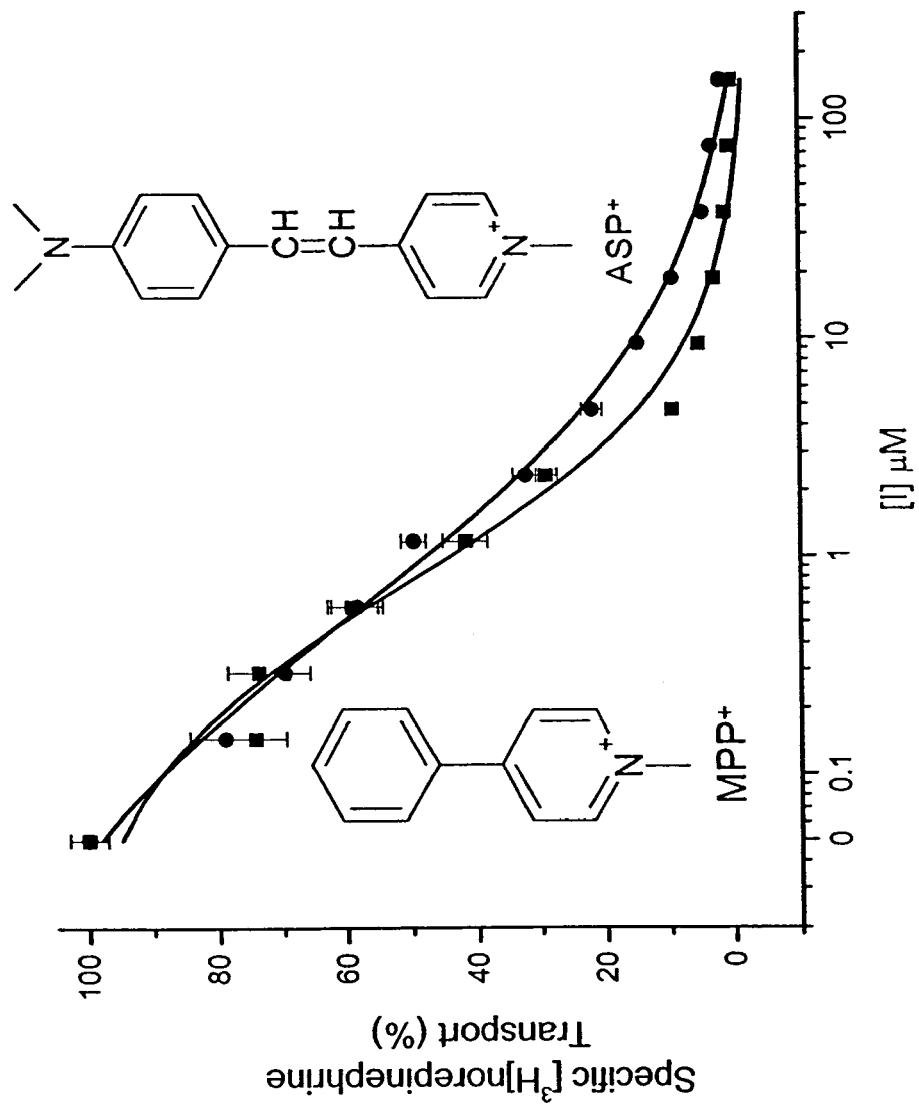
FIG. 1. $MPP^+$ and $ASP^+$ inhibit NE accumulation. [$^3$H]NE accumulation was measured in the hNET-transfected HEK-293 cells in the presence of increasing concentrations of $ASP^+$ or $MPP^+$ and normalized to similar data in the absence of an inhibitor. Non-specific activity was determined by application of 10 μM desipramine. The data were fit to NE transport remaining by the equation $y=100/(1+([I]/IC_{50})^n)$, where [I] is the concentration of $ASP^+$ or $MPP^+$ and $K_i$ values were determined using Cheng-Prusoff correction for substrate concentration. The fits yield $K_i$ ($ASP^+$)=780±77 nM and Ki ($MPP^+$)=600±67 nM. Values are represented as means±S.E.M., N=5.

Although neurotransmitter transporters are central to neuronal signal processing and have been implicated in various nervous system related disorders, the art lacks methods that effectively characterize neurotransmitter function and activity.

The present inventors have found that the fluorescent substrate 4-(4-dimethylaminostyrl)-N-methylpyridinium (ASP+) is transported by NET, DAT and SERT. The present inventors have developed methods to measure neurotransmitter transport mechanisms using ASP+ and fluorescence microscopy. The present inventors have shown that the ASP+ fluorescence assays provide mechanistic information about transport including the kinetics of the Na+- and Cl−-dependent transport and the kinetics involved in blockade of transport by antagonists.

Furthermore, the inventors have developed rapid screening methods that utilize fluorescent substrates such as ASP+ to identify modulators of neurotransmitter transporters. Pharmaceutical formulations of the modulators of neurotransmitter transporters identified by the methods of the present invention may be used to treat various nervous system disorders that are caused by defects in neurotransmitter uptake and retention mechanisms. Therefore, the invention also provides methods of treatment of nervous system disorders by using neurotransmitter transport modulators that are identified by the screening methods of the present invention.

A. ASP+

ASP+ [4-(4-(dimethylamino)styrl)-N-methyl-pyridinium] is a permanent, positively-charged fluorescent dye originally used for the vital staining of mitochondria and nerve terminals (Morozova et al., 1981). ASP+ fluoresces visible light and is a substrate for organic cation transporters (OCT) (Hohage etal., 1998; Stachon et al., 1996). ASP+ is structurally related to 1-methyl-1,2,3,6-tetrahydopyridinium (MPP), which is a neurotoxic metabolite of MPTP that induces dopamine transporter (DAT)-dependent neurotoxic degeneration of the substantial nigra (Gainetdinov et al., 1997).

Using time-resolved fluorescence microscopy, the present inventors have demonstrated ASP$^+$ accumulation in human embryonic kidney cells (HEK) expressing human norepinephrine (NE) transporters (hNET). ASP$^+$ accumulation has sub-μM potency for HNET, requires Na and Cl, is blocked by cocaine and desipramine, and is competed for by NE. The inventors have measured ASP$^+$ accumulation from single hNET-transfected HEK cells with a 50 msec time resolution. The present inventors have also shown that ASP$^+$ is also a substrate for the dopamine and serotonin transporters. It is contemplated that ASP$^+$ will also be useful in the study of epinephrine transport. ASP$^+$ fluorescent microscopy permits localization of transport activity in single cells and neuronal processes. The ASP$^+$ fluorescent microscopy methods of the invention also permits analysis of many cells, while retaining information about single cells. The ASP$^+$ fluorescence assays of the invention provide detailed mechanistic information about transport. For example, temporal and spatial resolution of transport, transport kinetics, affinity for substrate, turnover rates, surface expression, and binding constants may be measured. Furthermore, features such as voltage dependence of neurotransmitter accumulation can be assessed under voltage clamp using ASP$^+$ fluorescent microscopy.

B. Neurotransmitter Transporters

As described earlier, neurotransmitter transporters are responsible for the uptake of neurotransmitters from the synaptic cleft and thereby are responsible for the regulation of neurotransmission. Transporter proteins in the plasma membranes of neurons and glia also participate in vital nutrient and osmolyte acquisition. Neurotransmitter transporters are typically ion dependent, have high-affinity/specificity for one neurotransmitter, and are temperature and pH sensitive.

Chemical signaling by small molecule neurotransmitters, including DA, NE, E, SE (or 5HT), glutamate, glycine, and GABA, is terminated by transporter-mediated clearance (Rudnick and Clark, 1993). Disruption of transporter function, mediated by genetic mutations, pathological conditions or drugs of abuse, can elevate or rapidly decrease extracellular neurotransmitter levels, perturb presynaptic transmitter homeostasis, and trigger significant alterations in physiology and behavior (Giros et al., 1996; Pelham, 1997). For example, psychoactive agents such as cocaine and the amphetamines compete with the neurotransmitter substrates of the DA, NE, and SE transporters, and their addictive potential has been attributed to DAT blockade (Kuhar et al., 1991). In contrast, NET and SERT antagonists such as imipramine, desipramine, fluoxetine, and sertraline are important agents in the treatment of mood disorders, particularly depression (Barker and Blakely, 1996). Cloning and molecular analysis of neurotransmitter transporters has also shown that genetic mutations and variations are associated with some neuronal disorders and some forms of addictions to substances of abuse.

However, the study of neurotransmitter transporters is severely limited by methods that utilize radiolabeled neurotransmitters or fluorescent analogs of neurotransmitters, all of which have so far been incapable of distinguishing substrate binding from transport. The methods of the present invention provide better understanding of transport with a superior time and spatial resolution and at the level of a single cell, if required. Thus, the present methods provide better characterization of transport mechanics of transporters. This is also relevant in the case of diseases associated with mutations of neurotransmitter transporters as the methods will aid in better understanding the physiological basis of neuronal disorders caused by mutant transport molecules in comparison to normal molecules. The methods of the invention are also important with regard to providing a better understanding of transport changes caused by numerous addictive agents and therapeutic agents that target neurotransmitter transporters.

In addition, the screening methods of the invention, provide rapid screening and identification of novel modulators of neurotransmitter transport. Such assays are also beneficial for screening for modulators of mutant transporters that are expressed in patients with genetic neuronal disorders. It is contemplated that such methods will be useful in identifying therapeutic agents specifically tailored to treat an individual patient. As neurotransmitter transporters are also associated with addiction to drugs of abuse and alcohol the screening methods of the invention are contemplated to provide therapeutic agents that will be effective in reversing such addictions.

i. Norepinephrine Transporters (NET)

NET is a member of a large family of Na$^+$ and Cl$^-$ dependent transporters (Blakely et al., 1991; Masson et al., 1999), exhibits a sub-micromolar substrate potency and can concentrate NE against its concentration gradient. NET accumulates NE by coupling the substrate and co-transported ions at a proposed stoichiometry of 1NE/1Na$^{2+}$/1Cl$^-$ (Ressler and Nemeroff, 1999; Ramamoorthy et al., 1993; Bonisch and Harder, 1986).

Approximately 70-90% of the NE released into synapses is estimated to be cleared using NET. NE uptake by NET is competitively inhibited by various drugs of abuse such as amphetamine and cocaine, and antidepressants (e.g., desipramine, imipramine, venlafaxine, mirtazapine, reboxetine, bupropion), thereby resulting in an elevation of the synaptic concentrations of NE which results in potentiation of the activation of postsynaptic receptors. Other evidence has shown that treatments with drugs that alter noradrenergic transmission can cause an up- or downregulation of NET, which in turn causes changes in the sensitivity to endogenous catecholamines.

NET was isolated by expression cloning in 1991, and the gene was found to be located on human chromosome 16q 12.2 (Pacholczyk et al., 1991). The NET gene is encoded by 14 exons, which span 45 kb from the start to the stop codon (Porzgen et al., 1996). The nucleotide and deduced amino acid sequence of the transporter predict a protein of 617 amino acids, containing 12 membrane-spanning domains. The organization of the protein is highly homologous to that of other neurotransmitter transporters including those transporting dopamine, epinephrine, serotonin and gamma-aminobutyric acid (GABA), which are members of a family of sodium- and chloride-dependent transport proteins in the plasma membranes of neurons and glial cells. Analysis of the NET gene and protein has facilitated the investigation of its potential role in psychiatric and other neuronal disorders. At least 13 genetic variants of NET have been identified so far by methods such as single-stranded conformational polymorphism analysis (Stober et al., 1996; Samochowiec et al., 2001; Kitayama et al., 2001).

ii. ET

The neurotransmitter NE is converted to epinephrine (E or Epi) in some neuronal cells, such as sympathetic neurons, and released as the primary neurotransmitter. Blakely and colleagues have cloned an E transporter (ET) cDNA from the bullfrog (*Rana catesbiana*) paravertebral sympathetic ganglia and characterized its functional properties via heterologous expression in non-neuronal cells (Apparsundaram et al., 1997; Blakely and Apparsundaram, 1998). A 2514 bp cDNA corresponding to the frog ET (fET), was identified and sequence analysis revealed an open reading frame coding for a protein of 630 amino acids. The fET protein sequence has a 75, 66, and 48% amino acid identity with human NET, DAT, and SERT, respectively. Transfection of HeLa cells with fET confers $Na^+$- and $Cl^-$-dependent catecholamine uptake. Uptake of [$^3$H]NE by fET is inhibited by catecholamines in a stereospecific manner and fET-mediated transport of catecholamines was found to be sensitive to cocaine and other tricyclic antidepressants. Although the human ET has not yet been cloned, the methods of the present invention are envisioned to be effective to study the transport characteristics of any human protein that transports epinephrine.

iii. Dopamine Transporter (DAT)

The dopamine transporter (DAT) is a member of the subfamily of monoamine transporters with numerous common topological structures and significant amino acid sequence homology. DAT has been identified as located on the distal end of chromosome 5 (5p15.3) (Giros et al., 1992). Kawarai et al. (1997), isolated and characterized the human DAT gene (hDAT) including about 1 kb of 5'-flanking region. The hDAT gene spans over 64 kb, consisting of 15 exons separated by 14 introns. The intron-exon structure of the hDAT gene is most similar to that of the human NET gene. Promoter sequence analysis demonstrated a 'TATA'-less, 'CAT'-less and G+C-rich structure. Two E box and several Sp-1-binding sites exist in the promoter region. These structural features are similar to that of the human D1A dopamine receptor gene and the human monoamine oxidase A gene. The DAT gene encodes for a 620-amino acid protein with a calculated molecular weight of 68,517 (Giros et al., 1992) and is associated with numerous neuropsychiatric disorders (Bannon, 2001). Examples of neurological diseases involving dopamine transporter function include schizophrenia, addiction disorders, attention deficit hyperactivity disorder (ADHD), psychoses, Tourette's syndrome, or Parkinson's disease.

iv. SERT

The serotoninergic system modulates numerous behavioral and physiological functions and has been associated with control of mood, emotion, sleep and appetite. Synaptic serotonin (SE), also called 5-hydroxytryptamine or 5HT, concentration is controlled by the serotonin transporter (SERT) which is involved in reuptake of serotonin into the pre-synaptic terminal. The cloning of the human SERT protein by Ramamoorthy et al., (1993), shows that human SERT is encoded by a single gene that is localized to chromosome 17q11.1-17q12 and encodes for a 630-amino acid protein. The hSERT is a $Na^+$- and $Cl^-$-coupled serotonin transporter and has been found to be expressed on human neuronal, platelet, placental, and pulmonary membranes (Ramamoorthy et al., 1993).

The SERT has been associated with depression and anxiety (Soubrie, 1988; Barnes, 1988); obesity (Blundell, 1986; Silverstone et al., 1986); alcoholism (Gill et al., 1987; Naranjo et al., 1987); postanoxic intention myoclonus (Van Woert et al., 1976); acute and chronic pain (Le Bars, 1988); as well as sleep disorders (Koella, 1988). SERT has also been shown to mediate behavioral and/or toxic effects of cocaine and amphetamines (Ramamoorthy et al., 1993). A variety of specific serotonin reuptake inhibitors (SSRIs) such as fluoxetine and paroxetine have been developed for the treatment of depression (reviewed in Scholss, 1998). However, as Schloss points out, the art lacks a detailed understanding of the mode of action of these antidepressant drugs on their target, the SERT protein. Furthermore, although several drugs that target the SERT have been identified the art still lacks effective drugs for the treatment and alleviation of depression and other neurological disorders.

Recent research has shown that polymorphisms in the promoters of SERT's are a risk factor for susceptibility to depression (Neumeister et al., 2002). Other studies have also shown the association of variants of SERT's to other disorders. For example, association for allele 12 of the variable number tandem repeat (VNTR) in the second intron of the SERT gene and schizophrenic disorders has been shown (Tsai et al., 2002).

C. Methods of Measurement of Transport

The present invention provides methods for the measurement of transport of neurotransmitter transporters including the transporters for biogenic amines such as serotonin, dopamine, epinephrine, norepinephrine. It is contemplated that these methods are also applicable to transporters of the amino acids neurotransmitters such as L-glycine and L-glutamate, L-aspartate, and g-aminobutyric acid (GABA). In some embodiments, the present invention provides a novel and rapid method for analysis of transport by a neurotransmitter transporter that comprises the measurement of uptake and/or accumulation of $ASP^+$ that is specifically taken up by the transporter. The methods of measurement involve fluorescence microscopy. In other embodiments, other fluorescent substrates may be used, some of which are contemplated to be analogs of $ASP^+$ and others are contemplated to be analogs of other native neurotransmitters.

i. Microscopy

Fluorescent microscopy is used to measure transport using $ASP^+$ which is a fluorescent substrate for several neurotransmitter transporters. Cells that either endogenously or exogenously express a neurotransmitter are isolated and plated on glass bottom Petri-dishes or multi-well plates that may typically be coated with poly-L-lysine or any other cell adhesive agent. Cells are typically cultured for three or more days. The culture medium is then aspirated and the cells are mounted on a Zeiss 410 confocal microscope. During the confocal measurement cells remain without buffer for approximately thirty seconds. Background autofluorescence is established by collecting images for ten seconds prior to the addition of the buffer and $ASP^+$. As $ASP^+$ has a large Stoke shift between excitation ($1_{max}$=488 nm) and emission maxima ($1_{max}$=610 nm), the argon laser is tuned to 488 nm and the emitted light filtered with a 580-630 nm band pass filter ($1_{max}$=610 nm). The substantial red shift can be exploited to reduce background auto-fluorescence produced in the absence of substrate. The gain (contrast) and offset (brightness) for the photomultiplier tube (PMT) may be set to avoid detector saturation at the higher $ASP^+$ concentrations that may be used in certain experiments. The effects of photo-bleaching on $ASP^+$ accumulation may also be determined by examining the rate of $ASP^+$ accumulation and decay at various acquisition rates. In a constant pool of $ASP^+$, rates as high as 20 Hz (50 msec/image) can be set.

ii. Fluorescence Anisotropy Measurements

To evaluate $ASP^+$ binding to the surface membranes, cells expressing a neurotransmitter transporter may be exposed to ASP with horizontal polarizer (see, for example, as in FIG. 5C), with the polarizer rapidly switching to the vertical position. Cells may be imaged with alternating polarizations for 3 minutes to measure light intensity in the horizontal ($I_h$) and vertical ($I_v$) positions in order to calculate the anisotropy ratio, $r=(I_v-gI_h)/(I_v+2gI_h)$. The factor g may be determined by using a half wave plate as described by Blackman et al. (1996). In this formulation, r=0.4 implies an immobile light source. Surface anisotropy can be measured at the cell circumference over 1 pixel width (0.625 mm). Cytosolic anisotropy can be measured near the center of the cell, approximately 5 pixel widths from the membrane.

iii. Image Analysis

The fluorescent images may be processed using suitable software. For example, fluorescent images were processed using MetaMorph imaging software (Universal Imaging Corporation, Downington PA). Fluorescent accumulation was established by measuring the average pixel intensity of time resolved fluorescent images within a specified region identified by the DIC image. Average pixel intensity is used to normalize among cells.

iv. Single Cell Fluorescence Microscopy

In some embodiments, the invention provides measurement of transporter characteristics at the single-cell level. Single-cell fluorescence microscopy provides a powerful assay to study rapid neurotransmitter uptake kinetics from single cells.

V. Automation

Figures 11A, 11B:
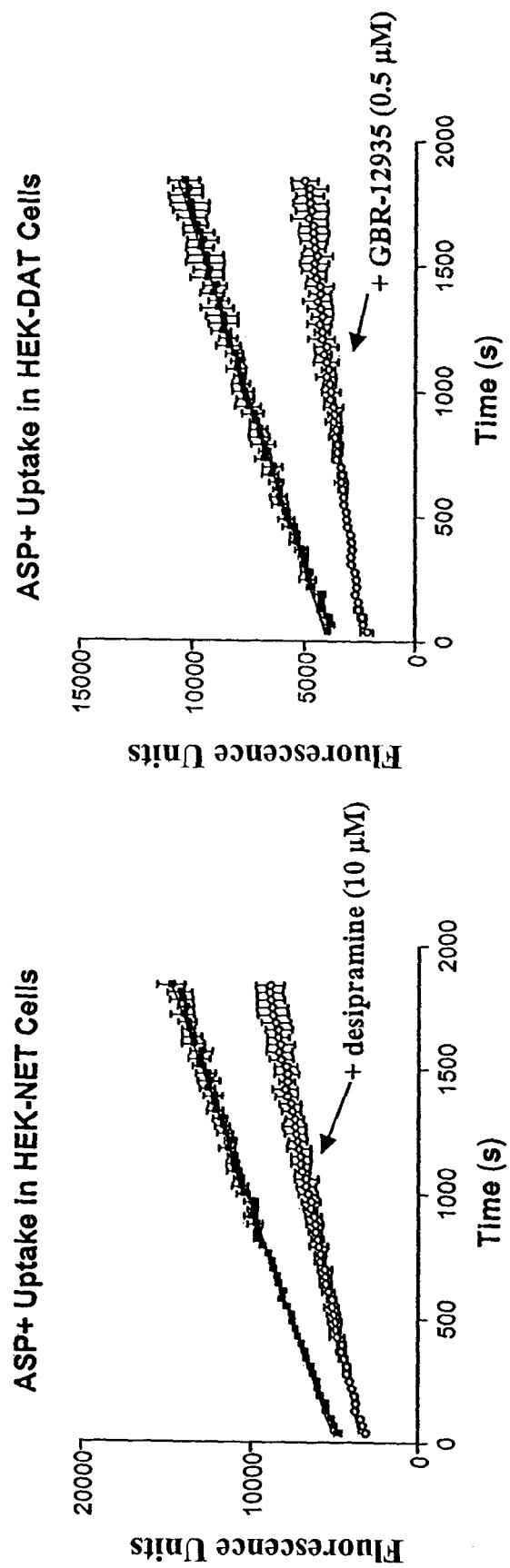
FIGS. 11A-11B. ASP+ accumulation in transfected cells is blocked by monoamine transporter antagonists. Transport assays with ASP+ on the FLEXstation were performed either with or without competing antagonists. Desipramine, a NET-specific antagonist, blocked accumulation of ASP+ by NET (FIG. 11A), whereas GBR-12935, a specific DAT antagonist blocked ASP+ accumulation by DAT (FIG. 11B).

The inventors further contemplate that all methods disclosed herein are adaptable to high-throughput formats using robotic fluid dispensers, multi-well formats and fluorescent plate readers for the identification of neurotransmitter transport modulators. Examples are provided in Example 3 and FIGS. 9-11.

vi. Other Methods

In addition, uptake and accumulation of the neurotransmitter may be also characterized by other methods known in the art such as (a) in vivo inhibition by known agonists and antagonists of the neurotransmitter transporter; (b) knockout models, where a particular gene that modulates in or otherwise suspected to be involved in transport is omitted (for example, DAT knockouts as described in Giros et al., 1996) (c) slice electrophysiology, in which particular neurons are identified and subjected to analysis in situ.

D. Screening For Neurotransmitter Modulators

Defects in neurotransmitter transporters are associated with various nervous system disorders including depression, stress disorders, attention deficit disorder, Parkinson's disease, anxiety, obesity, several sleep related disorders and certain neurodegenerative diseases (Edwards, 1993). For example, biogenic amine transporters which are responsible for inactivation of dopamine, norepinephrine, serotonin and epinephrine are major targets for multiple psychoactive substances including cocaine, amphetamines, methylphenidate (Ritalin™), tricyclic antidepressants and the SSRIs such as fluoxetine (Prozac™). However, there is still a need in the art to identify other modulators of neurotransmitter transporters given the large number of neurological and psychiatric diseases that are associated with transporter defects.

The present invention provides methods for identifying modulators of the function of neurotransmitter transporters. These methods may comprise random screening of large libraries of candidate substances. Alternatively, the methods may be used to focus on particular classes of compounds selected with an eye towards structural attributes that are believed to make them more likely to modulate the function of a particular neurotransmitter transporter.

By function, it is meant that one may assay for uptake, accumulation, or clearance of the neurotransmitter, its analog or derivative or for some biological aspect of neurotransmitter release, uptake or clearance. Micro-dialysis and amperometry may be used to assay transporter finction in vivo (Giros et al., 1996; Galli et al. 1998).

To identify a neurotransmitter transporter modulator, one generally will determine the finction of the neurotransmitter transporter in the presence and absence of the candidate agent, a modulator defined as any agent that alters function. For example, a method generally comprises:

a) providing a candidate modulator;

b) contacting the candidate modulator with a cell expressing a neurotransmitter transporter, or a cell extract or cell membrane preparation that comprises the neurotransmitter transporter, or a suitable experimental animal;

c) measuring one or more characteristics of the transporter, cell, cell extract or cell membrane preparation, or animal, that reflects the function or activity of the transporter; and d) comparing the characteristic measured in step (c) with the characteristic of the transporter, cell, cell extract or cell membrane preparation, or animal in the absence of the candidate modulator, wherein a difference between the measured characteristics indicates that the candidate modulator is, indeed, a modulator of the neurotransmitter transporter.

Comparing the characteristic measured as described in the steps above includes measurement of uptake, accumulation, binding, ion dependence, antagonist block, dependence on expression level, voltage- and $Ca^{2+}$-dependence, or clearance of $ASP^+$ or other fluorescent substrate that is specifically taken up by the neurotransmitter transporter.

Assays may be conducted in cell free systems such as cellular extracts, cell membrane preparations which may be prepared by lysing cells, in isolated cells, in cells that express endogenous a neurotransmitter transporter, in cells that are genetically engineered to express a neurotransmitter transporter, in cells that exogenously or endogenously express mutant or functionally deficient transporters, or in organisms including transgenic animals or animal models of diseases wherein the disease is associated with neurotransmitter transporters. Thus, knockouts for neurotransmitter transporters may be used (Giros et al., 1996; Sora et al., 2001). It will, of course, be understood that all the screening methods of the present invention are useful in themselves notwithstanding the fact that effective candidates may not be found. The invention provides methods for screening for such candidates, not solely methods of finding them.

i. Modulators

As used herein the term "candidate substance" or "candidate agent" refers to any molecule that may potentially inhibit or enhance the activity of a neurotransmitter transporter. The candidate substance may be a protein or fragment thereof, a small molecule, or even a nucleic acid molecule. It may prove to be the case that the most useful pharmacological compounds will be compounds that are structurally related to the known neurotransmitter transporter modulators, agonists and antagonists such as cocaine, amphetamines, monoamine oxidase inhibitors, imipramine and the like. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate agents may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on the neurotransmitter transporter. Regardless of the type of inhibitor or activator identified by the present screening methods, the effect of the inhibition or activation by such a compound results in a difference as compared to that observed in the absence of the added candidate substance.

ii. In vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay in this invention is the use of cellular extracts that comprise a neurotransmitter, these may be cell membrane preparations that comprise a neurotransmitter transporter.

Another example is a cell-binding assay. While not directly addressing finction, the ability of a modulator to bind to a target molecule (in this case the neurotransmitter transporter) in a specific fashion is strong evidence of a related biological effect. For example, binding of a molecule to a neurotransmitter transporter may, in and of itself, be inhibitory, due to steric, allosteric or charge-charge interactions. The neurotransmitter transporter protein may be either free in solution, fixed to a support, expressed in or on the surface of a cell. Either the neurotransmitter transporter or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

iii. In cyto Assays

The present invention also contemplates the screening of agents for their ability to modulate neurotransmitter transporter in cells. Various cells and cell lines can be utilized for such screening assays as long as the cell expresses a neurotransmitter transporter. This includes cells specifically engineered to expresses a neurotransmitter transporter. Such cells and nucleic acid vectors are described in several sections infra as well as U.S. Pat. Nos. 5,312,734, 5,418,162, and 5,424,185, the contents of which are all incorporated herein by reference.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

iv. In vivo Assays

In vivo assays involve the use of various animal models, including transgenic animals that have been engineered to have specific defects, or carry markers that can be used to measure the ability of a candidate agent to reach and effect expression of neurotransmitter transporters in different cells within the organism. Due to their size, ease of handling, and information on their physiology and genetic make-up, mice and/or *C. elegans* are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate agents are administered to an animal, and the ability of the candidate agent(s) to alter one or more characteristics that are a result of neurotransmitter finction or activity, as compared to a similar animal not treated with the candidate agent(s), identifies a modulator. The characteristics may be any of those discussed above with regard to the finction of a particular neurotransmitter such as change in neurotransmission, change in the activity of some other downstream protein due to a change in neurotransmission, or instead a broader indication such as behavior of an animal etc.

The present invention provides methods of screening for candidate agents that modulate neurotransmitter transporter finction or activity. In these embodiments, the present invention is directed to a method for determining the ability of a candidate agent to modulate neurotransmitter transporter finction, generally including the steps of: administering a candidate substance to the animal; and determining the ability of the candidate substance to change one or more characteristics of the neurotransmitter transporter.

Methods for in vivo imaging using $ASP^+$ are described in Herrera and Banner (1990), and in Herrera et al., (1990), (both incorporated herein by reference). In situ methods for analysis of $ASP^+$ are described in Pietruck & Ullrich, (1995) and Rohlicek & Ullrich, (1994), (also incorporated herein by reference). These methods may be suitably modified with the other teachings of this specification to perform the in vivo assays.

Treatment of these animals with test agents will involve the administration of the agent, in an appropriate form, to the animal. Administration will be by any route that could be utilized for clinical or non-clinical purposes, including but not limited to oral, nasal, buccal, or even topical. Alternatively, administration may be by parenteral methods such as intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

F. Vectors for Delivery and Expression of Neurotransmitter Transporters

Within certain embodiments, expression vectors are employed to express a neurotransmitter transporter in a cell, for example, an DAT, NET, ET, or SERT. The specification provides a description of transformation of HEK cells to express exogenous NET as one example infra. Furthermore, U.S. Pat. Nos. 5,312,734, 5,418,162, and 5,424,185, all incorporated herein by reference, describe nucleic acids, vectors, and host cells used to express various neurotransmitter transporters in cells. As will be understood by one of skill in the art, the invention is not limited to any particular type of neurotransmitter transporter or cell type and expression vectors encoding any neurotransmitter transporter can be used in any cell type. Additionally, as set forth above one may also use mutant versions, isoforms, and other variants of any neurotransmitter transporter in the methods of the invention. The foregoing section provides a general description of how exogenous expression may be achieved.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

i. Regulatory Elements

Throughout this application, the term "expression construct" is meant to include any type of genetic construct containing a nucleic acid coding for a gene product in which part or all of the nucleic acid encoding sequence is capable of being transcribed and translated into a polypeptide product. An "expression cassette" is defined as a nucleic acid encoding a gene product under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 1 and 2 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $α_1$-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., |

TABLE 1-continued

Promoter and/or Enhancer

| Promoter/Enhancer | References |
|---|---|
| | 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

ii. Selectable Markers

In certain embodiments of the invention, the cells contain nucleic acid constructs encoding a neurotransmitter transporter may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

iii. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

iv. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

V. Delivery of Expression Vectors

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

a. Adenovirus

One of the methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shutoff(Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by AdS DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MO1) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell innoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus & Horwitz, 1992; Graham and Prevec, 1991). Recently, animal studies suggested that recombinant adenovirus could be used for gene therapy (Stratford-Perricaudet & Perricaudet, 1991; Stratford-Perricaudet et al., 1990; Rich et al., 1993). Studies in administering recombinant adenovirus to different tissues include trachea instillation (Rosenfeld et al, 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

b. Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact- sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

c. Adeno-Associated Viruses

Adeno-associated virus (AAV) is an attractive virus for delivering foreign genes to mammalian cells or subjects (Ridgeway, 1988; Baichwal and Sugden, 1986; Hermonat and Muzycska, 1984). AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided by U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector of the present invention can be obtained by restriction endonuclease digestion of AAV or a plasmid such as p201, which contains a modified AAV genome (Samulski et al., 1987). Alternatively, the terminal repeats may be obtained by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

d. Other Viruses

Other viral vectors may be employed as expression constructs in the present invention. Vectors derived from viruses such as vaccinia virus (Ridgeway, 1988; Baichwal and Sugden, 1986; Coupar et a., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1989, 1991) recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

e. Non-Viral Methods

Several non-viral methods for the transfer of expression constructs into mammalian cells also are contemplated by the present invention. These include DEAE-dextran (Gopal, 1985), electroporation (Tur-Kaspa et al., 1986; Potter et al., 1984), direct microinjection (Harland and Weintraub, 1985), lipofectamine-DNA complexes, cell sonication (Fechheimer et al., 1987), and receptor-mediated transfection (Wu and Wu, 1987; Wu and Wu, 1988).

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

f. Liposomes

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are Lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0 273 085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells.

G. Pharmaceutical Formulations

As the present invention provides clinical methods for the treatment of neurological diseases using the modulators of neurotransmitter transporters identified by the screening methods of the invention, it will be necessary to prepare pharmaceutical compositions comprising the therapeutic modulatory agent(s) in a form appropriate for the intended application. Generally, this will entail preparing compositions that are essentially free of pyrogens, as well as other impurities that could be harmful to humans or animals.

One will generally desire to employ appropriate salts and buffers. Aqueous compositions of the present invention comprise an effective amount of the neurotransmitter transporter modulator dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Supplementary active ingredients also can be incorporated into the compositions.

Administration of these compositions according to the present invention will be via any common route so long as the target tissue is available via that route. This includes administration may be by systemic or parenteral methods including intravenous injection, intracerebral, intradermal, subcutaneous, intramuscular, intraperitoneal methods. Direct administration by local injection into the site of disease is also contemplated. Depending on the nature of the modulator administration may also be via oral, nasal, buccal, rectal, vaginal or topical. Such compositions would normally be administered as pharmaceutically acceptable compositions, described supra.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The composition may be formulated as a "unit dose." For example, one unit dose could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

H. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell Culture

HEK-293 cells were maintained in DMEM with 10% FBS (v/v), 2 mM glutamine, 100 I.U./mL penicillin and 100 µg/mL streptomycin (Gibco). The human norepinephrine transporter (HEK-hNET) and human serotonin transporter (HEK-hSERT) stable cells line were previously described (Galli et al., 1995; Ramamoorthy, 1998). The human dopamine transporter (HEK-hDAT) cells were also used.

Radiolabled Transport Assay

All accumulation studies were performed at room temperature (22° C.) unless otherwise indicated. HEK-hNET cells were plated on poly-L-lysine coated 24-well tissue culture plates at $10^5$ cells per well three days prior to performing transport assays. The cells were at approximately 90% confluence on the third day. The medium was removed by aspiration. Cells were then pre-incubated for 10 min in Krebs-Ringer's-Hepes (KRH: in mM 130 NaCl, 1.3 KCl, 2.2 $CaCl_2$, 1.2 $MgSO_4$, 1.2 $KH_2PO_4$, 10 Hepes, and 1.8 g/L glucose, pH 7.4) medium with or without 10 µM desipramine. Desipramine, a specific NET blocker, was used to establish nonspecific activity in hNET cells. Pargyline (10 µM) and ascorbic acid (10 µM) were added to prevent metabolism and oxidation of NE, respectively. The assay mixture was aspirated after 10 minutes and cells were washed three times with 4° C. KRH buffer. Accumulated [$^3$H]NE was determined by liquid scintillation of 1% (w/v) sodium dodecylsulphate solubilized cells.

Primary Tissue Culture

SCG neurons were dissociated by trituration followed by digestion with 0.25% trypsin and 0.3% collagenase. Non-neuronal cells were removed by preplating on uncoated, Falcon 60 mm plates. Neurons were cultured on poly-L-ornithine/laminin/poly D-lysine coated MatTek Dishes at a density of 3000-4000 cells/well in F-14$^+$ media containing 5% fetal calf serum, 2 mM L-glutamine, 60 ng/ml progesterone, 16 mg/ml putrescine, 400 ng/ml L-thyroxine, 38 ng/ml sodium selenite, 340 ng/ml tri-iodothyroxine, 5 mg/ml insulin, penicillin/streptomycin, 10 µM fluorodeoxyuridine and 20 ng/ml NGF. The neurons were maintained for 3-5 days in the presence of NGF before use.

Microscopy

HEK-hNET cells were plated on 35 mm glass bottom Petri-dishes (MatTek, Ashland, Mass.) coated with poly-L-lysine three days prior to experimentation. The culture medium was aspirated, cells were immediately mounted on a Zeiss 410 confocal microscope and the microscope was focused on the center of the monolayer of cells. During the confocal measurment cells remain without buffer for approximately thirty seconds. Background autoflourescence was established by collecting images for ten seconds prior to the addition of KRH (see Radiolabeled Transport),1.8 mg/L Glucose, 10 µM ascorbic acid, 10 µM pargalyine, 10 µM tropolone (Sigma, Boulder CO), and ASP$^+$. The argon laser was tuned to 488 nm; the emitted light was filtered with a 580-630 nm band pass filter ($\lambda_{max}$=610 nm). ASP$^+$ has a large Stoke shift between excitation ($\lambda_{max}$=488 nm) and emission maxima ($\lambda_{max}$=610 nm). The substantial red shift can be exploited to reduce background autofluorescence produced in the absence of substrate. The gain (contrast), offset (brightness) for the photomultiplier tube (PMT) was set to avoid detector saturation at the highest ASP$^+$ concentration used in the transport. The effects of photobleaching on ASP$^+$ accumulation were determined by examining the rate of ASP$^+$ fluorescence at various acquisition rates. Acquisition rates greater than 0.3 Hz degraded ASP$^+$, and the inventors set the fastest test acquisition rate at 12 Hz (80 msec/image).

Fluorescence Anisotropy Measurements

To evaluate ASP$^+$ binding to the surface membranes, HEK-hNET cells were exposed to 2 µM ASP$^+$ with horizontal polarizer (FIG. 5C), with the polarizer rapidly switching to the vertical position. Cells were imaged with alternating polarizations for 3 minutes to measure light intensity in the horizontal ($I_h$) and vertical ($I_v$) positions in order to calculate the anisotropy ratio, $r=(I_v-gI_h)/(I_v+2\ g\ I_h)$. The factor g was determined by using a half wave plate as described by Blackman et al. (1996). In this formulation, r =0.4 implies an immobile source (Smith et al., 1999). Surface anisotropy was measured from the cell circumference, taken as 1 pixel width. Cytosolic anisotropy was measured near the center of the cell, approximately 5 pixel widths from the membrane.

Image Analysis

The fluorescent images were processed using MetaMorph imaging software (Universal Imaging Corporation, Downington Pa.). Fluorescent accumulation was established by measuring the average pixel intensity of time resolved fluorescent images within a specified region; regions of interest are identified by the DIC image. Average pixel intensity is used to normalize between cells of different sizes. Parental (HEK-293) cells possess endogenous mechanisms for ASP$^+$ accumulation, therefore, NET mediated ASP$^+$ accumulation is defined as the fluorescence of HEK-hNET cells minus the fluorescence of HEK-293cells. All cells are subtracted against auto-fluorescence.

Example 2

ASP$^+$ Uptake by NET, DAT & SERT

In the present Example the inventors demonstrate that the fluorescent molecule, ASP$^+$, is a substrate for NET, DAT and SERT. The inventors have shown that cells exogenously expressing NET, SERT and DAT accumulate ASP$^+$ over parental HEK-293 cells, indicating the use of ASP$^+$ as a powerful tool for the investigation of neurotransmitter transporters, especially the monoamine transporters. Although this example describes specific details and measurements with regard to NET, one of skill in the art will realize that similar analysis can be performed on DAT, SERT as well as ET. The present invention contemplates quantifying ASP$^+$ fluorescence to estimate NET, DAT, SERT and ET turnover rates, surface expression, and binding constants in transfected cells, and further investigation of neurons in tissue culture to study endogenous NET regulation and function.

Although ASP$^+$ is structurally disimilar to the endogenous substrate, it competes for specific NET-mediated NE transport. Temporal and spacial information on NET activity show that ASP$^+$ accumulation kinetics for the slow phase (phase II) is similar to radiolabeled NE accumulation kinetics. Spatial patterning and temperature dependence indicate that the rapid phase I represents ASP$^+$ binding to NET and the slow phase II represents transport. Moreover, measuring transport in single neurons, ordinarily impossible in single mammalian cells, is readily achieved with ASP$^+$. ASP$^+$ accumulation demonstrated a punctated pattern similar to NET distribution determined by immunohistochemistry (Schroeter et al., 2000). The fluorescent microscopy methods, used herein, also permit analysis of many cells, while retaining information about single cells.

MPP and ASP$^+$ Inhibit NE Accumulation

To test whether ASP$^+$ interacts with hNET, the inventors initially exposed HEK-hNET cells to increasing concentrations of ASP$^+$ in the presence of constant amounts of radiolabled NE. MPP was used as a control, as MPP is a known substrate for NET (Smith and Levi, 1999) and because MPP has a structure similar to ASP$^+$ (FIG. 1). Increasing MPP or ASP$^+$ inhibits radiolabeled NE accumulation. The inhibition constant ($K_i$) values for MPP$^+$ and ASP$^+$ were 600±67 nM and 780±77 nM (n=5), respectively; thus MPP$^+$ and ASP$^+$ potently interact with HEK-hNET cells in the sub μM range.

Cells that Express hNET Accumulate ASP$^+$

Confocal slices through the monolayer (FIGS. 2A, 2B & 2C, lower panels) show that ASP$^+$ accumulation in HEK-HNET divides into two phases: a rapid phase I ensues immediately after ASP$^+$ addition and appears localized to the cell surface (S) followed by a slower phase II localized to the cell interior (I). Concomitant differential interference contrast (FIGS. 2A, 2B & 2C, upper panels) help specify the confocal images. In the first three seconds after adding ASP$^+$ (FIG. 2B), the cell surface is noticeably bright, in certain locations, while the internal compartment remains devoid of ASP$^+$. As the cell interior becomes brighter and begins to fill in surface brightness remains constant. These qualitative features are also observed in DAT- and SERT-transfected cells. However, the response to ASP$^+$ is more robust in hNET-transfected cells, as illustrated in FIGS. 3A-3L. The weakest responder is SERT (FIGS. 3G-3I), but nonetheless significantly above parental cells (FIGS. 3J-3K). The remainder of this example describes only data with hNET-transfected cells.

Figure 4:
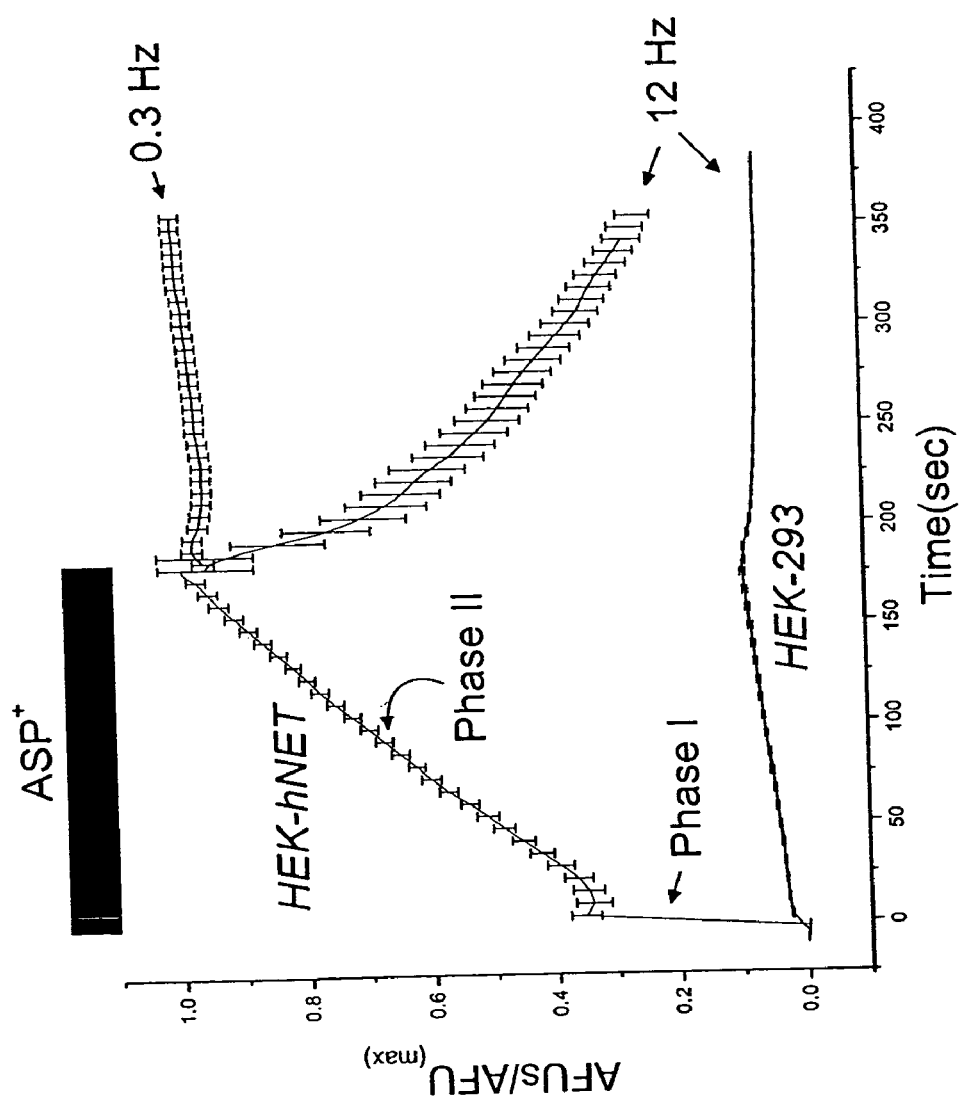
FIG. 4. ASP+ photo-bleaching. Transfected HEK-HNET and parental HEK-293 cells were exposed to 2 mM ASP+ for 180 sec followed by a wash. Images were taken from at least 40 individual cells per dish (cells defined by the corresponding DIC image) from 4 separate dishes. The average pixel intensity±S.E.M over all cells is plotted on the y-axis in arbitrary fluorescence units (AFUs). After ASP+ was removed, photo-bleaching was assessed at 0.3 Hz and 12 Hz for hNET-293 cells and 12 Hz for HEK-293 cells. Similar data were obtained up to 20 Hz and normalized to the fluorescence intensity maximums before and after ASP+ removal.

FIG. 4 shows that acquiring fluorescence data at 0.3 Hz (or lower), phase II accumulation is arrested immediately after removing ASP$^+$. Although the total intensity decreases due to ASP removal, the normalized data demonstrate sequestered ASP$^+$ remains constant. Because ASP$^+$ binds mitochondria (Stachon et al., 1996), the inventors contemplate that the flux is unidirectional and that cells retain the substrate after it enters the cell. Acquiring data at 12 Hz (or higher) results in a decline in brightness due to photobleaching. The decay time constant is linearly proportional to the acquisition rate and likely represents ASP$^+$ photo-bleaching, also observed in the absence of cells. Photo-bleaching thus sets a limit on the frequency of image acquisition, which under present conditions is 50 ms. Accumulation in the presence of ASP$^+$ is independent of sampling rate up to 20 Hz, permitting analysis of phase I during the first 3 seconds following ASP$^+$ application. HEK-293 cells also demonstrate phase I and II; however, both the rapid and slow accumulation phase are far less intense in parental than in transfected cells.

Phase I Represents ASP$^+$ Binding; Phase II Represents ASP$^+$ Transport

Figures 2A, 2B, 2C:
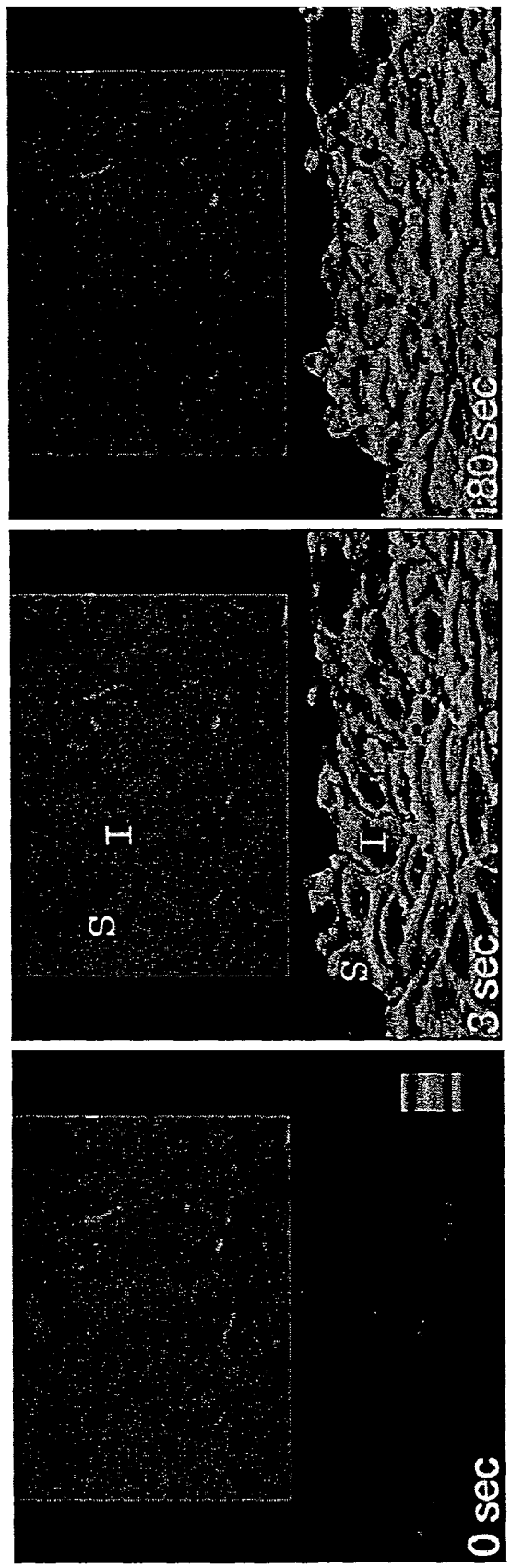
FIGS. 2A-2C. Cells expressing NET accumulate $ASP^+$. Single cells are visualized by DIC microscopy (top row) and accumulation is measured by an increase in $ASP^+$ fluorescence under confocal microscopy (bottom row). Images were taken at 0, 3 and 180 seconds after exposure to 800 nM $ASP^+$ (FIGS. 2A, 2B & 2C). In the upper panels, fluorescence images were projected onto the DIC image of the corresponding cells to identify cells surface (S) and interior (I). The color gradient represented in FIG. 2A denotes the $ASP^+$ intensity values (red being most intense).
Figures 3A, 3B, 3C, 3D, 3E, 3F, 3G, 3H, 3I, 3J, 3K, 3L:
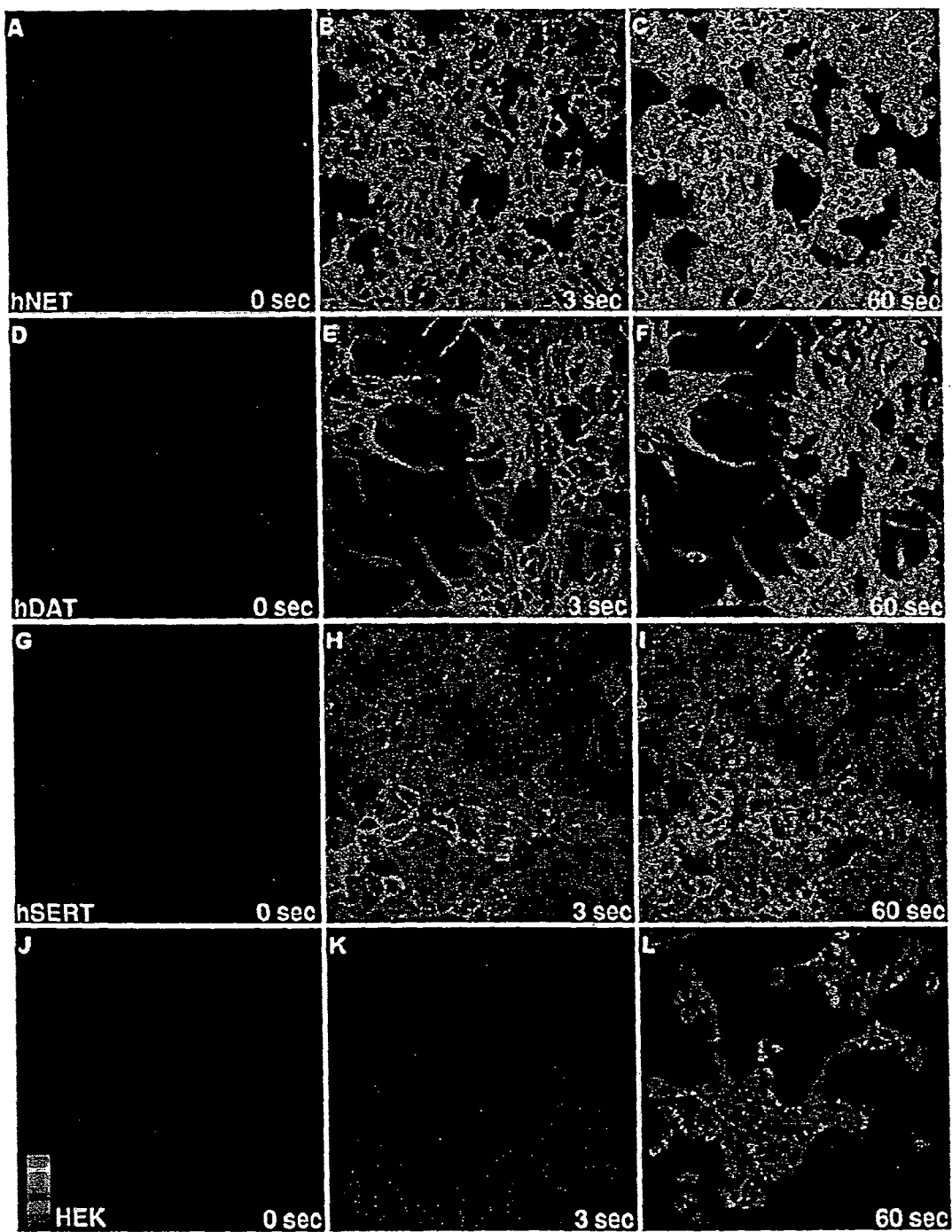
FIGS. 3A-3L. Monoamine transporters interact with ASP+. Like HEK-hNET cells hDAT and hSERT transfected cells accumulate ASP+. hNET (FIGS. 3A, 3B & 3C), hDAT (FIGS. 3D, 3E & 3F), hSERT (FIGS. 3G, 3H & 3I) and HEK-293 (FIGS. 3J, 3K & 3L) were exposed to 2 mM ASP for the times indicated in FIGS. 3J, 3K & 3L. The color gradient represented in FIG. 3J denotes the corresponding ASP+ intensity values.
Figure 5A:
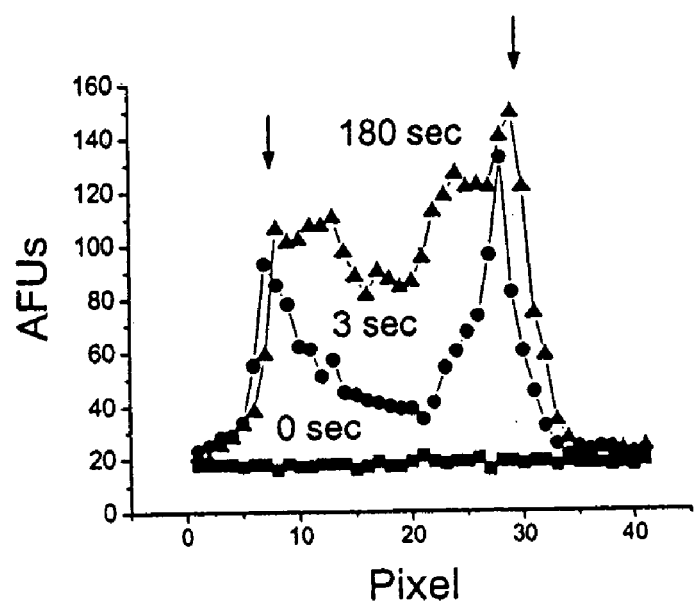
FIGS. 5A-5D. Phase I represents ASP+ binding; phase II represents ASP+ transport. Line scans across the center of HEK-hNET (FIG. 5A) and HEK-293 (FIG. 5B) cells were taken at 0, 3 and 180 seconds after exposure to 2 mM ASP+. Phase I, which refers to the initial increase in fluorescence as identified in DIC images, is localized to the cell surface (arrows), and the slower phase II registers with the cytosol (between arrows).
Figure 5B:
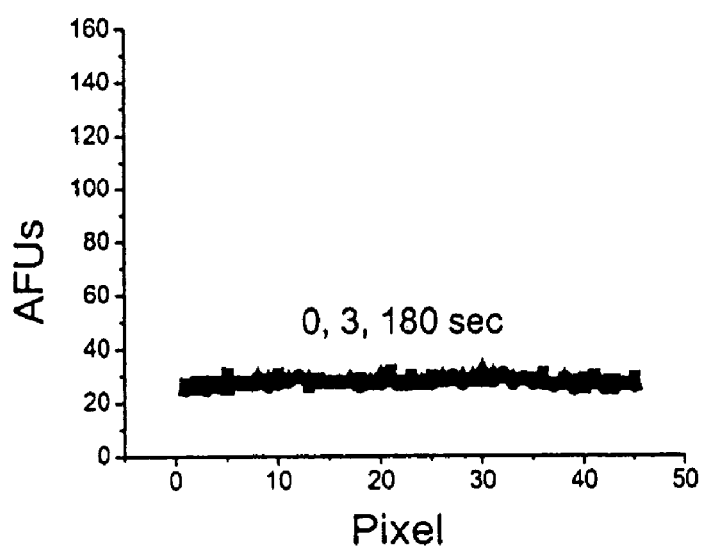
Figure 5C:
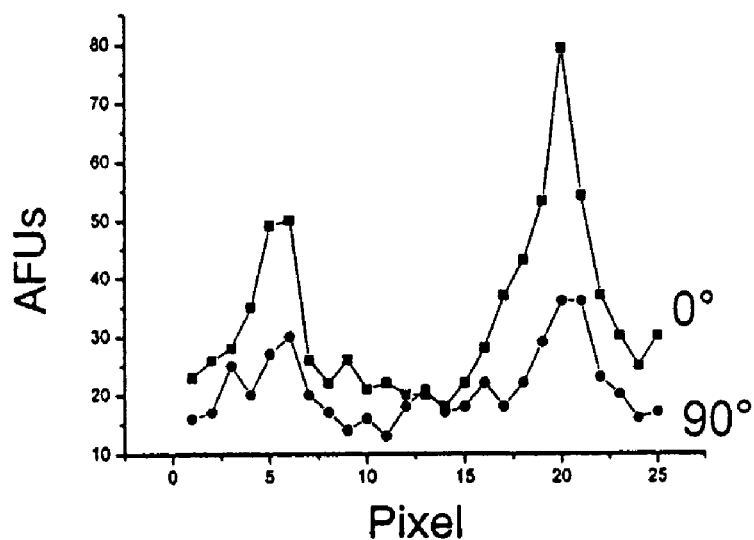
Figure 5D:
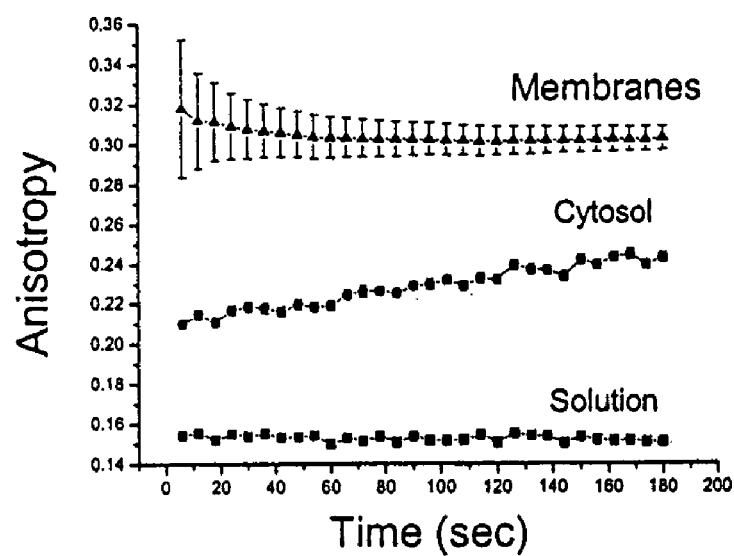

A line scan across individual cells at different times, as shown in FIG. 5A. corroborates that phase I is localized to the cell surface, as suggested in FIGS. 2A-2C. Notice that rapid accumulation, which peaks at the cell edges (arrows), remains essentially constant between 3 and 180 sec., whereas brightness at the cell center (between arrows) gradually increases over this same period. Furthermore, accumulation at the center occurs at the same rate as phase II (compare phase II slope in FIG. 4 with center elevation in FIG. 5A). HEK-293 cells subjected to similar line scans do not display similarly localized fluorescence (FIG. 5B). These data indicate that phase I represents a surface interaction with hNET and phase II represents ASP$^+$ transport. To test this interpretation the inventors measured the anisotropy of light from cell edges and cell centers. Light from the cell surface demonstrates significant divergence between horizontal (0°) and vertical (90°) polarization, whereas light from the center is less divergent (FIG. 5C). From these data the fluorescence anisotropy can be calculated (see description supra in section entitled Materials and Methods) across the line scan (FIG. 5D). The fluorescence anisotropy demonstrates that light from the edge emits from an effectively immobile source (0.30 <r <0.32) compared with the center (0.21<r<0.24). Solution ASP$^+$ shows even lower anisotropy (0.15). These data indicate two populations of the fluorescent compound: 1) a rapidly immobilize ASP$^+$ located near the cell surface, and 2) a slowly evolving, mobile pool in the interior, which represent the transported molecules.

To segregate the bound and transported populations of ASP$^+$ molecules, a potent blocker of NE transport, desipramine (DS), was administered. As seen qualitatively by comparing FIG. 6A (without DS) and FIG. 6B (with DS), the blocker virtually eliminates phase I ASP$^+$. Because mitochondria sequester intracellular ASP$^+$ it remains constant inside the cell after DS inhibition of transport. If DS interrupts transport at any time during phase II (arrows), the decrease in fluorescence is approximately equal to the amplitude of phase I (FIG. 6 C). The amount of ASP$^+$ that is sequestered after DS block (bottom slope) increases linearly over time and is parallel to the rate of phase II transport. The binding was also found to be less sensitive to temperature than transport (DeOliveara et al., 1989), indicating that cold temperature affects phase I less than it affects phase II. This is demonstrated in FIG. 6D. Furthermore, the biphasic phase I and phase II pattern does not represent transporter endocytosis as NET-mediated ASP accumulation is unaffected by a thirty-minute pre-incubation with concanavilin A or 0.45 mM sucrose. These data demonstrate that the initial rapid phase I measures ASP$^+$ binding, and that the slower phase II represents ASP$^+$ transport.

ASP$^+$ Pharmacology

To test whether ASP$^+$ has pharmacological properties similar to HNET HEK-hNET cells were pre-incubated for ten minutes with 10 μM desipramine, 10 μM cocaine or 30 μM NE (Galli et al., 1995). After pre-incubation with inhibitor alone, 2 μM ASP$^+$ was added to the inhibitor solution. In FIG. 7A, data are separated into phase I and II as previously described. Compared with injected cells, phase I is a considerably smaller in non-injected cells and insignificant in the presence of cocaine or DS, or in the presence of competing NE. Cl⁻ replacement enhances phase I, whereas Na⁺ replacement does not significantly alter phase I. Likewise, phase II is abridged in HEK-293 cells. Phase II is also reduced in the presence of competing NE and is insignificant in the presence of cocaine. However, whereas Na replacement dramatically reduces phase II to DS-insensitive levels, Cl is less effective. Gramicidin, which reduces the chemical gradients for Na and Cl (White, 1977), was administered at an intermediate concentration of 10 mg/mL given 15 min. before ASP⁺. Gramicidin reduces the slope of both phases. Finally, phase I and phase II saturate at similar ASP⁺ bath concentrations and have similar Michaelis-Menton constants, although ASP is slightly more potent for phase I (FIGS. 7B & 7C). Phase I: Vmax=10.5±0.94 AFUs/sec, Km=850±186 nM and n=1.15±0.30; phase II: Vmax=0.3235 0.014 AFUs/sec, Km=480±60 nM and n=1.51±0.35). The above parameters derived from ASP⁺ accumulation are comparable to those obtained with the endogenous substrate, NE, underscoring ASP⁺ s utility as a measure of NET activity.

ASP⁺ Accumulates in SCG Neurons

The interactions of ASP⁺ with NET in primary tissue culture neurons were also examined. Superior cervical ganglia (SCG) neurons endogenously express NET (Schroeter et al., 2000); therefore, dissociated SCG nerve cells were exposed to 2 μM ASP⁺ after the cells were pre-incubated for 10 minutes in the presence or absence of 10 μM desipramine. SCG neurons also contain OCT, which likely contributes to total ASP⁺ accumulation; however, DS inhibits NET at 10 μM without affecting OCT activity (Wu et al., 2000). The difference between ASP⁺ accumulation in the absence and presence of desipramine establishes specific NET-mediated ASP⁺ accumulation in SCG neurons (see FIG. 8A). As seen in FIGS. 8B and 8C, ASP⁺ accumulation in the cell body was similar to HNET-HEK cells, but accumulation in the neurite was punctuate, similar to hNET immunohistochemical staining (Schroeter et al., 2000). Thus ASP⁺ is amenable to the investigation of NET not only in transfected cells but also affords spatial resolution of transport activity in cultured neurons.

Example 3

Automation of Assays

Figure 9:
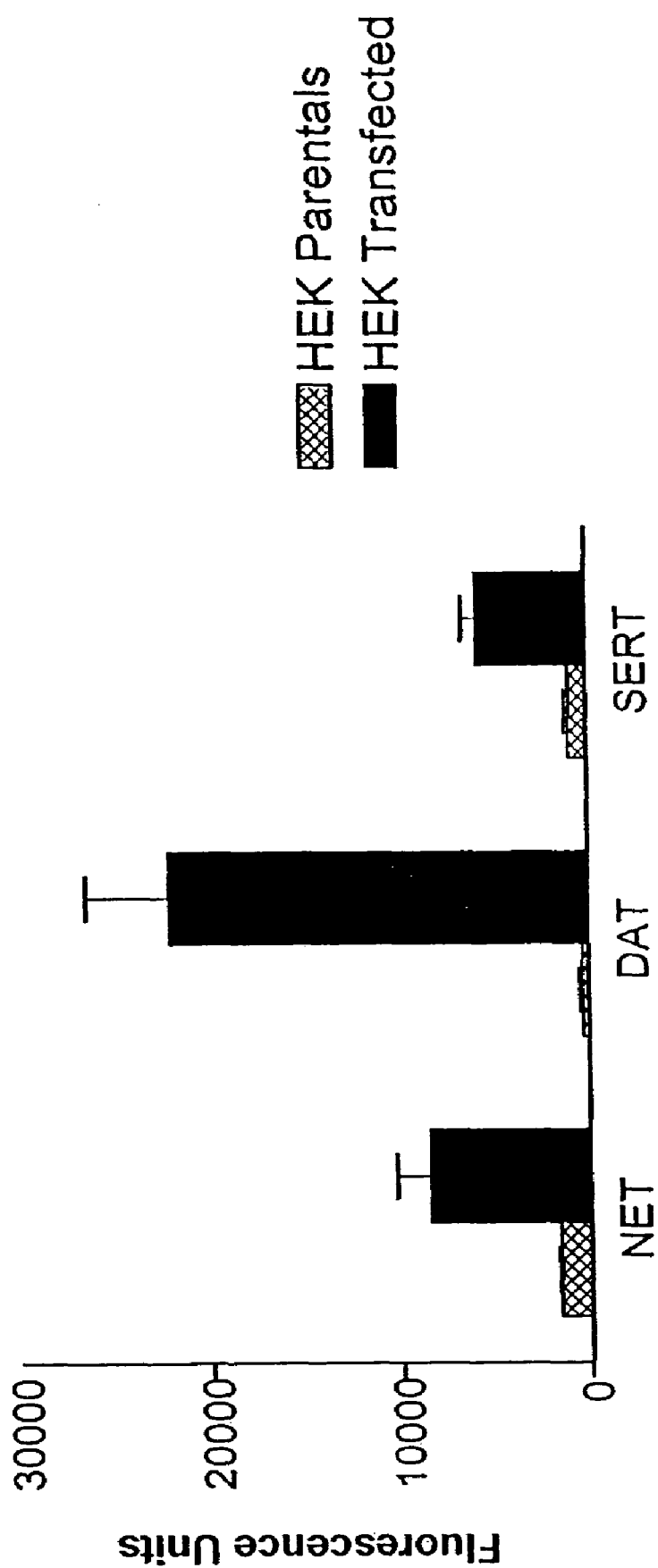
FIG. 9. Evidence of accumulation of ASP+ by monoamine transporters in transfected HEK-293 cells. Cells were plated in 96 well multiwell dishes and exposed to ASP+ in the presence of the external quencher Trypan Blue. ASP+ addition was performed using the. robotic fluid delivery abilities of the FLEXstation (Molecular Devices) and the amount of ASP+ accumulation determined at 15 minutes on the Flexstation. An equal number of parental and transfected cells were compared in parallel.

In the present Example the inventors have shown that the methods for measuring transport as well as the screening methods can be automated to achieve high-throughput analysis of data. Results of this are depicted in FIG. 9, FIG. 10, and FIG. 11.

Cell Culture

HEK-293 cells (American Type Culture Collection, Manassas, Va.) and HEK-293 cells stably transfected with SERT, NET, or DAT (Qian et al, 1997) were maintained in monolayer culture at 37° C., 5% $CO_2$ in Dulbecco's modified Eagle's medium (DMEM) containing 10% fetal bovine serum, 2 mM glutamine, 100 units/ml penicillin, and 100 μg/ml streptomycin. Medium for the transfected lines was supplemented with G418 (250 μg/ml). Trypsin, glutamine, penicillin, streptomycin, G418, and phosphate-free DMEM were purchased from Life Technologies, Inc. or obtained from the Vanderbilt Media Core. For all transport assays, cells were plated on poly-D-lysine (0.1 mg/ml)-coated (0.1 mg/ml)-coated 96-well plates. HEK cells were plated at 12,500 cells per well in 96 well plates, HEK-DAT cells were plated at 15,000 cells per well, HEK-NET cells were plated at 20,000 per well, and HEK-SERT cells were plated at 20,000 cells per well in a volume of 200 uL. HEK, HEK-DAT, and HEK-SERT cells were grown for 48 hours and HEK-NET cells were grown for 72 hours to a confluency of ~90%.

ASP⁺ Uptake Assays

ASP⁺ was obtained from Molecular Probes, Inc. and dissolved in KRH buffer to indicated concentrations. Trypan Blue was obtained from Sigma as a 0.4% solution and diluted to a final concentration of 30 uM in KRH buffer.

To limit the time delay between the addition of ASP⁺ and the measurement of accumulation of ASP⁺ during the kinetic assays, plates were divided in half and assayed one half at a time. At assay, the medium was removed from wells in the first 6 columns by aspiration, and the cells were incubated with Trypan Blue in KRH buffer for 20 minutes at 37° C.in room air. Then, medium was removed from the wells in the last 6 columns and replaced with Trypan Blue in KRH buffer. Inhibitors were added to appropriate wells and cells were again incubated at 37° C. in room air. After incubation, ASP⁺ was added to the first 6 columns in 20 μL aliquots at indicated concentrations and accumulated fluorescence measured and recorded over time by the FLEXStation ultilizing SoftMax Pro Software. Then, ASP⁺ was added to the last 6 columns and fluorescence accumulation measured and recorded. Specific uptake was determined by subtracting the amount of accumulated ASP⁺ in the presence of 10 μM Paroxetine, 10 μM final of desipramine, or 0.5 μM of GBR 12909 or GBR 12935 for SERT, NET, and DAT, respectively. Measures were done in quadruplicate and duplicate in the absence or presence of inhibitors, respectively. Data from wells treated with inhibitor were averaged and subtracted from data from untreated wells. Subtracted data for each concentration of ASP⁺ was plotted versus time in Graphpad Prism and fit with a linear equation to determine the rate of uptake. Rate of uptake for at least 3 experiments were averaged and plotted versus concentration. Data was fit with a one-site binding equation to determine $K_m$ and $V_{max}$ values.

Endpoint assays were conducted to evaluate the sensitivity of ASP⁺ uptake to transporter antagonists. At assay, the media was removed by aspiration and replaced with Trypan Blue in KRH buffer. Inhibitors of SERT, NE and DAT were added at the indicated concentrations. Cells were incubated at 37° C. for 10 minutes in room air. The assay was initiated by the addition of 3 μM ASP⁺. ASP⁺ accumulation was measured after 10 minutes. Specific uptake was determined by subtracting the amount of accumulated ASP⁺ in the presence of saturating amounts of inhibitors such as 10 μM Paroxetine, 10 μM final of desipramine, or 0.5 μM of GBR 12909 or GBR 12935 for SERT, NET, and DAT, respectively. Measures were done in quadruplicate, and the subtracted values were averaged. Uptake was plotted against the logarithmic values of inhibitor concentration and fitted with a one-site competition curve to determine $IC_{50}$ values. $K_i$ values were then calculated using the Cheng-Prusoff equation. The results for the above described assays are set forth in FIG. 9, FIG. 10A, FIG. 10B, FIG. 10C, FIG. 11A and FIG. 11B.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,252,479
U.S. Pat. No. 5,312,734
U.S. Pat. No. 5,418,162
U.S. Pat. No. 5,424,185
U.S. Pat. No. 5,424,195
U.S. Pat. No. 5,670,113
U.S. Pat. No. 6,127,133
Angel et al., *Mol. Cell. Biol.*, 7:2256, 1987.
Angel et al., *Cell*, 49:729, 1987b.
Angel et al., *Mol. Cell. Biol.*, 7:2256, 1987a.
Apparsundaram et al., *J. Neurosci.*, 17(8):2691-2702, 1997.
Aston-Jones et al., *Biol. Psychiatry*, 46:1309-1320, 1999.
Atchison and Perry, *Cell*, 46:253, 1986.
Atchison and Perry, *Cell*, 48:121, 1987.
Ausubel et al., In: *Current Protocols in Molecular Biology*, John, Wiley and Sons, Inc, New York, 1994.
Axelrod and Kopin, *Prog. Brain Res.*, 31, 21-32, 1969.
Baichwal and Sugden, In: *Gene Transfer*, Kucherlapati (ed.), New York, Plenum Press, 117-148, 1986.
Banerji et al., *Cell*, 27(2 Pt 1):299-308, 1981.
Banerji et al., *Cell*, 33(3):729-740, 1983.
Bannon, Eur. *Neuropsychopharmacol.*, 11(6):449-55, 2001.
Barker and Blakely, *Mol. Pharmacol.*, 50(4):957-65, 1996.
Barnes, *Science*, 241:1029-1030, 1988.
Benvenisty and Neshif, *Proc. Natl. Acad. Sci. USA*, 83(24): 9551-9555, 1986.
Berkhout et al., *Cell*, 59:273-282, 1989.
Biederman and Spencer, *Biol. Psychiatry*, 46:1234-1242, 1999.
Blakely and Apparsundaram, *Adv. Pharmacol.*, 42:206-210, 1998.
Blakely et al., *Nature*, 354:66-70, 1991.
Blanar et al., EMBO J., 8:1139, 1989.
Blundell, *Appetite*, 7(1):39-56 1986.
Bodine and Ley, *EMBO J.*, 6:2997, 1987.
Bonisch and Harder, *Naunyn Schmiedebergs Arch. Pharmacol.*, 334:403-411, 1986.
Bonisch, *Naunyn Schmiedebergs Arch. Pharmacol.*, 327: 267-272, 1984.
Boshart et al., *Cell*, 41:521, 1985.
Bosze et al., *EMBO J.*, 5(7):1615-1623, 1986.
Braddock et al., *Cell*, 58:269, 1989.
Bruns, *Methods Enzymol.*, 296:593-607, 1998.
Bulla and Siddiqui, *J. Virol.*, 62:1437, 1986.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Celander and Haseltine, *J. Virology*, 61:269, 1987.
Celander etal., *J. Virology*, 62:1314, 1988.
Chandler et al., *Cell*, 33:489, 1983.
Chang et al., *Hepatology*, 14:134A, 1991.
Chang et al., *Mol. Cell. Biol.*, 9:2153, 1989.
Chatterjee et al., *Proc Natl. Acad Sci. USA*, 86:9114, 1989.
Choi et al., *Cell*, 53:519, 1988.
Clarkson et al., *Circulation*, 87:950-962, 1993.
Coffin, In: *Virology*, Fields et al., eds., Raven Press, New York, 1437-1500, 1990.
Cohen et al., *J. Cell. Physiol.*, 5:75, 1987.
Corey et al., *Proc. Natl. Acad. Sci. USA*, 91:1188-1192, 1994.
Costa et al., *Mol. Cell. Biol.*, 8:81, 1988.
Couch et al., *Am. Rev. Resp. Dis.*, 88:394-403, 1963.
Coull et al., *Neuroimage*, 10:705-715, 1999.
Coupar et al., *Gene*, 68:1-10, 1988.
Cripe et al, *EMBO J.*, 6:3745, 1987.
Culotta and Hamer, *Mol. Cell. Biol.*, 9:1376, 1989.
Dandolo et al., *J. Virology*, 47:55-64, 1983.
De Oliveira et al., *Neuropharmacology*, 28:823-828, 1989.
De Villiers et al., *Nature*, 312(5991):242-246, 1984.
DeFelice and Galli, *Adv. Pharmacol.*, 42:186-190, 1998.
Deschamps et al., *Science*, 230:1174-1177, 1985.
Dow and Kline, *Ann. Clin. Psychiatry*, 9:1-5, 1997.
Dubensky et al., *Proc. Natl. Acad. Sci. USA*, 81:7529-7533, 1984.
Edbrooke et al., *Mol. Cell. BioL*, 9:1908, 1989.
Edlund et al., *Science*, 230:912-916, 1985.
Edwards, *Ann Neurol.*, November; 34(5):63 8-45, 1993.
European Appl. EPO 0 273 085
Fechheimer et al., *Proc. Natl. Acad. Sci. USA*, 84:8463-8467, 1987.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Fleckenstein et al., *Eur. J. Pharmacol.*, 382:45-49, 1999.
Foecking and Hofstetter, *Gene*, 45(1):101-105, 1986.
Friedmann, *Science*, 244:1275-1281, 1989.
Fujita et al., *Cell*, 49:357, 1987.
Gainetdinov et al., *J. Neurochem.*, 69:1322-1325, 1997.
Galli et al., *J. Exp. Biol.*, 198(10):2197-2212, 1995.
Galli et al., *PNAS*, 93:8671-8676, 1998.
Ghosh and Bachhawat, In: *Liver Diseases, Targeted Diagnosis and Therapy Using Specific Receptors and Ligands*. Wu et al., eds., Marcel Dekker, New York, pp. 87-104, 1991.
Ghosh-Choudhury et al., *EMBO J.*, 6:1733-1739, 1987.
Gill et al., *Alcoholism II*, 444-449, 1987.
Gilles et al., *Cell*, 33:717, 1983.
Giros et al., *Mol. Pharmacol.*, 42(3):383-390, 1992.
Giros et al., *Nature*, 379(6566):606-612, 1996.
Glassman et al., *J. Nerv. Ment. Dis.*, 173:573-576, 1985.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, *Mol. CellBiol.*, 5:1188-1190, 1985.
Graham and Prevec, In: *Methods in Molecular Biology: Gene Transfer and Expression Protocol*, Murray (Ed.), Humana Press, Clifton, N.J., 7:109-128, 1991.
Graham et al., *J. Gen. Virl.*, 36(1):59-74, 1977.
Greene et al., *Immunology Today*, 10:272, 1989
Grosschedl and Baltimore, *Cell*, 41:885, 1985.
Grunhaus et al., *Seminar in Virology*, 200(2):535-546, 1992.
Hadrich et al., *J. Med. Chem.*, 42:3101-3108, 1999.
Harland and Weintraub, *J. Cell Biol.*, 101:1094-1099, 1985.
Hartzell, *J. Cell Biol.*, 86:6-20, 1980.

Haslinger and Karin, *Proc. Natl. Acad. Sci. USA*, 82:8572, 1985.
Hatfield and McGaugh, *Neurobiol. Learn. Mem.*, 71:232-239, 1999.
Hauber and Cullen, *J. Virology*, 62:673, 1988.
Hen et al., *Nature*, 321:249, 1986.
Hensel et al., *Lymphokine Res.*, 8:347, 1989.
Hennonat and Muzycska, *Proc. Natl. Acad. Sci. USA*, 81:6466-6470, 1984.
Herr and Clarke, *Cell*, 45:461, 1986.
Herrera and Banner, *J. Neurocytol.*, 19:67-83, 1990.
Herrera et al., *J. Neurocytol.*, 19:85-99, 1990.
Hersdorffer et al., *DNA Cell Biol.*, 9:713-723, 1990.
Herz and Gerard, *Proc. Natl. Acad. Sci. USA*, 90:2812-2816, 1993.
Hirochika et al., *J. Virology*, 61:2599, 1987.
Hirsch et al., *Mol. Cell. Biol.*, 10:1959, 1990.
Hohage et al., *J. Pharmacol. Exp. Ther.*, 286:305-310, 1998.
Holbrook et al., *J. Virology*, 157:211, 1987.
Horlick and Benfield, *Mol. Cell. Biol.*, 9:2396, 1989.
Horwich et al., *J. Virology*, 64:642-650, 1990.
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawaetal., *Cell*, 51:251, 1987.
Imbra and Karin, *Nature*, 323:555, 1986.
Imler et al., *Mol. Cell. Biol*, 7:2558, 1987.
Imperiale and Nevins, *Mol. Cell. Biol.*, 4:875, 1984.
Iversen et al., *J. Pharmacol. Exp. Ther.*, 157:509-516, 1967.
Jacob et al., *Circulation*, 99:1706-1712, 1999.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. BioL*, 9:3393, 1989.
Jones and Shenk, *Cell*, 13:181-188, 1978.
Jones, *Prog. Brain Res.*, 88:381-394, 1991.
Kadesch and Berg, *Mol. Cell. Biol.*, 6:2593, 1986.
Kaneda et al., *Science*, 243:375-378, 1989.
Karin et al., *Mol. Cell. Biol.*, 7:606, 1987.
Karlsson et al., *EMBO J.*, 5:2377-2385, 1986.
Katinka et al., *Cell*, 20:393, 1980.
Kato et al., *J. Biol. Chem.*, 266:3361-3364, 1991.
Kawamoto et al., *Mol. Cell. Biol.*, 8:267, 1988.
Kawarai et al., *Gene*, Aug 11;195(1):11-8 1997.
Kiledjian et al., *Mol. Cell. Biol.*, 8:145, 1988.
Kitayama et al., *Neurosci. Lett.*, 312(2):108-112, 2001.
Klamut et al., *Mol. Cell. Biol.*, 10:193, 1990.
Koch et al., *Mol. Cell. Biol.*, 9:303, 1989.
Koella, *Neuronal Serotonin*, Osborne et al. (eds.), 153-170, 1988.
Kriegler and Botchan, In: *Eukaryotic Viral Vectors*, Gluzman, ed., Cold Spring Harbor:
Cold Spring Harbor Laboratory, N.Y., 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhar et al., *Trends Neurosci.*, 14(7):299-302, 1991.
Kuhl et al., *Cell*, 50:1057, 1987.
Kunz et al., *Nucl. Acids Res.*, 17:1121, 1989.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Le Bars, *Neuronal Serotonin*, Osborne and Hamin (eds), 171-229, 1988.
Le Gal La Salle et al., *Science*, 259:988-990, 1993.
Lee et al., *Nature*, 294:228, 1981.
Lee et al., *Nucleic Acids Res.*, 12:4191-206, 1984.
Levinson et al., *Nature*, 295:79, 1982.
Levrero et al., *Gene*, 101: 195-202, 1991.
Lin et al., *Mol. Cell. Biol.*, 10:850, 1990.
Luria et al., *EMBO J.*, 6:3307, 1987.
Lusky and Botchan, *Proc Natl. Acad. Sci. USA*, 83:3609, 1986.
Lusky et al., *Mol. Cell. Biol.* 3:1108, 1983.
Majors and Varnus, *Proc. Natl. Acad. Sci. USA*, 80:5866, 1983.
Maniatis, et al., Molecular Cloning, A Laboratory Manual, Cold Spring Harbor Press, Cold Spring Harbor, N.Y., 1988.
Mann et al., *Cell*, 33:153-159, 1983.
Markowitz et al., *J. Virol.*, 62:1120-1124, 1988.
Masson et al., *Pharmacol. Rev.*, 51:439-464, 1999.
McNeall et al., *Gene*, 76:81, 1989.
Miksicek et al., *Cell*, 46:203, 1986.
Mordacq and Linzer, *Genes and Dev.*, 3:760, 1989.
Moreau et al., *Nucl. Acids Res.*, 9:6047, 1981.
Morozova et al., *Tsitologiia*, 23(8):916-923, 1981.
Muesing et al., *Cell*, 48:691, 1987.
Mulligan, *Science*, 260:926-932, 1993.
Naranjo et al., *Clin. PharmacoL Ther.*, 41:266-274, 1987.
Neumeister et al., *Arch. Gen. Psychiatry*, 59(7):613-620, 2002.
Ng et al., *Nuc. Acids Res.*, 17:601, 1989.
Nicolas and Rubenstein, In: *Vectors: A survey of molecular cloning vectors and their uses*, Rodriguez and Denhardt (eds.), Stoneham: Butterworth, pp. 493-513, 1988.
Nicolau et al., *Methods Enzymol.*, 149:157-176, 1987.
Ondek et al., *EMBO J.*, 6:1017, 1987.
Ornitz et al., *Mol. Cell. Biol.*, 7:3466, 1987.
Pacholczyk et al., *Nature*, March 28;350(6316):350-4, 1991.
Palmiter et al., *Nature*, 300:611, 1982.
Paskind et al., *Virology*, 67:242-248, 1975.
Pech et al., *Mol. Cell. Biol.*, 9:396, 1989.
Pelham, *Nature*, 389(6646):17, 19, 1997.
Perales et al., *Proc. Natl. Acad. Sci. USA*, 91:4086-4090, 1994.
Perez-Stable and Constantini, *Mol. Cell. Biol.*, 10:1116, 1990.
Picard and Schaffner, *Nature*, 307:83, 1984.
Pietruck and Ullrich, *Kidney Int.*, 47(6):1647-1657, 1995.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Porzgen et al., *Biochem Biophys Res Commun.*, 227(2):642-643, 1996.
Potter et al., *Proc. Natl. Acad. Sci. USA*, 81:7161-7165, 1984.
Prasad and Amara, *J. Neurosci.*, 21:7561-7567, 2001.
Queen and Baltimore, *Cell*, 35:741, 1983.
Quinn et al., *Mol. Cell. Biol.*, 9:4713, 1989.
Racher et al., *Biotechnology Techniques*, 9:169-174, 1995.
Ragot et al., *Nature*, 361:647-650, 1993.
Rarnamoorthy et al., *Am. J. Obstet. Gynecol.*, 173:1782-1787, 1995.
Ramamoorthy et al., *Biochemistry*, 32:1346-1353, 1993.
Ramamoorthy et al., *J. Biol. Chem.*, 273:2458-2466, 1998.
Ramamoorthy et al., *Proc Natl Acad Sci., USA*, March 15;90(6):2542-6, 1993.
Redondo et al., *Science*, 247:1225, 1990.
Reisman and Rotter, *Mol. Cell. Biol.*, 9:3571, 1989.
Remington's Pharmaceutical Sciences, 15th ed., pages 1035-1038 and 1570-1580, Mack Publishing Company, Easton, Pa., 1980.
Renan, *Radiother. Oncol.*, 19:197-218, 1990.

Resendez Jr. et al., *Mol. Cell. Biol.*, 8:4579, 1988.
Ressler and Nemeroff, *Biol. Psychiatry*, 46:1219-1233, 1999.
Rich et al., *Hum. Gene Ther.*, 4:461-476, 1993.
Ridgeway, In: *Vectors: A survey of molecular cloning vectors and their uses*, Stoneham: Butterworth, pp. 467-492, 1988.
Ripe et al., *Mol. Cell. Biol.*, 9:2224, 1989.
Rittling et al., *Nuc. Acids Res.*, 17:1619, 1989.
Rohlicek and Ullrich, *Ren. Physiol. Biochem.*, 17(2):57-61, 1994.
Rosen et al., *Cell*, 41:813, 1988.
Rosenfeld etal., *Cell*, 68:143-155,1992.
Rosenfeld etal., *Science*, 252:431-434, 1991.
Roux et al., *Proc. Natl. Acad. Sci. USA*, 86:9079-9083, 1989.
Rudnick and Clark, Biochim. Biophys. Acta, 1144(3):249-63, 1993.
Sakai et al., *Genes and Dev.*, 2:1144, 1988.
Sambrook et al., In: *Molecular Cloning: A Laboratory Manual*, 2nd Ed., Cold Spring Harbor Press, Cold Spring Harbor, N.Y., 1989.
Samochowiec et al., *Neuropsychobiology*, 43(4):248-253, 2001.
Samulski et al., *J. Virol.*, 61(10):3096-3101, 1987.
Satake et al., *J. Virology*, 62:970, 1988.
Schaffner et al., *J. Mol. Biol.*, 201:81, 1988.
Schloss, *Psychopharmacol.*, 1998;12(2):115-21
Schroeter et al., *J. Comp. Neurol.*, 420:211-232, 2000.
Searle et al., *Mol. Cell. BioL*, 5:1480, 1985.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Silverstone et al., *Appetite*, 7 Supple., pp. 85-97, 1986.
Skrebitsky and Chepkova, *Rev. Neurosci.*, 9:243-264, 1998.
Sleigh and Lockett, *J. EMBO*, 4:3831, 1985.
Smith and Levi, *J. Pharmacol. Exp. Ther.*, 291:456-463, 1999.
Sora et al., *Proc Natl Acad Sci USA.*, Apr 24;98(9):5300-5, 2001.
Soubrie, In: *Neuronal Serotonin*, Osborne and Hamon (eds.), 255-270 1988.
Southwick et al., *Biol. Psychiatry*, 46:1192-1204, 1999.
Spalholz et al., *Cell*, 42:183, 1985.
Spandau and Lee, *J. Virology*, 62:427, 1988.
Spandidos and Wilkie, *EMBO J.*, 2:1193, 1983.
Stachon et al., *Cellular Physiol. Biochem.*, 6:72-91, 1996.
Stephens and Hentschel, *Biochem. J.*, 248:1, 1987.
Stober et al., Lancet., 347(9011):1340-1341, 1996.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (ed.), New York: Plenum Press, pp. 149-188, 1986.
Thiesen et al., *J. Virology*, 62:614, 1988.
Top et al., *J. Infect. Dis.*, 124:155-160, 1971.
Treisman, *Cell*, 42:889, 1985.
Tronche et al., *Mol. Biol. Med.*, 7:173, 1990.
Trudel and Constantini, *Genes and Dev.* 6:954, 1987.
Tsai et al., *Neuropsychobiology*, 45(3):131-133, 2002.
Tur-Kaspa et al., *Mol. Cell Biol.*, 6:716-718, 1986.
Tyndell et al., *Nuc. Acids. Res.*, 9:6231, 1981.
Van Woert, M. H. et al., *Monogr. Neural. Sci.*, 3:71-80, 1976.
Vannice and Levinson, *J. Virology*, 62:1305, 1988.
Varmus et al., *Cell*, 25:23-36, 1981.
Vasseur et al., *Proc. Natl. Acad. Sci. USA*, 77:1068, 1980.
Wagner et al., *Proc. Natl. Acad. Sci. USA* 87(9):3410-3414, 1990.
Wang and Calame, *Cell*, 47:241, 1986.
Watanabe et al., *Jpn. Heart J.*, 22:977-985, 1981.
Weber et al., *Cell*, 36:983, 1984.
Weinberger et al., *Mol. Cell. Biol.*, 8:988, 1984.
Winoto and Baltimore, *Cell*, 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Wu et al., *Biochim. Biophys. Acta.*, 1466:315-327, 2000.
Yutzey et al., *Mol. Cell. Biol.*, 9:1397, 1989.

What is claimed is:

1. A method for measuring monamine neurotransmitter transport in a cell or cellular extract comprising:
    a) providing a cell that expresses a monoamine neurotransmitter transporter or a cellular extract that comprises a monoamine neurotransmitter transporter;
    b) exposing the cell or the extract to $ASP^+$; and
    c) measuring the transport of $ASP^+$;
    thereby measuring the transport of the monoamine neurotransmitter in the cell.

2. The method of claim 1, wherein measuring transport further comprises measuring the kinetics of the monoamine neurotransmitter transporter.

3. The method of claim 1, wherein measuring transport is in real time.

4. The method of claim 1, wherein measuring the transport of $ASP^+$ is by fluorescence microscopy or using a fluorescent plate reader.

5. The method of claim 1, wherein the time resolution of measuring transport is 1 hour to 50 milliseconds.

6. The method of claim 1, wherein the cell is a neuronal cell.

7. The method of claim 1, wherein the cell is a blood platelet.

8. The method of claim 1, wherein the cell is a placental cell.

9. The method of claim 1, wherein the cell is a trophoblast.

10. The method of claim 1, wherein the monoamine neurotransmitter transporter is an endogenously expressed transporter.

11. The method of claim 1, wherein the monoamine neurotransmitter transporter is an exogenously expressed transporter.

12. The method of claim 1, wherein the monoamine neurotransmitter transporter is a norepinephrine transporter.

13. The method of claim 1, wherein the monoamine neurotransmitter transporter is an epinephrine transporter.

14. The method of claim 1, wherein the monoamine neurotransmitter transporter is a dopamine transporter.

15. The method of claim 1, wherein the monoamine neurotransmitter transporter is a serotonin transporter.

16. A method of screening for agents that can modulate the activity of a monoamine neurotransmitter transporter comprising:

a) providing a cell or cell extract that expresses a monoamine neurotransmitter transporter;

b) exposing said cell or cell extract to an agent that is a candidate monoamine neurotransmitter transporter modulator;

c) exposing the cell or cell extract to $ASP^+$;

d) measuring the transport of $ASP^+$; and e) comparing the transport of $ASP^+$ in said cell to the transport of $ASP^+$ in a cell or cell extract that has not been exposed to the agent;

thereby determining if the agent is a modulator of activity of said monoamine neurotransmitter transporter.

17. The method of claim 16, further comprising the use of a fluorescent plate reader to provide high-throughput screening of agents.

18. The method of claim 16, wherein the monoamine neurotransmitter transporter is a norepinephrine transporter, an epinephrine transporter, a dopamine transporter or a serotonin transporter.

19. The method of claim 16, wherein said method is an in vivo method.

20. The method of claim 16, wherein said method is an in vitro method.

21. The method of claim 16, wherein measuring the transport of $ASP^+$ further comprises adding a quencher and measuring the polarization of light in the presence and absence of the agent.

* * * * *

UNITED STATES PATENT AND TRADEMARK OFFICE
CERTIFICATE OF CORRECTION

PATENT NO. : 7,318,917 B2 Page 1 of 1
APPLICATION NO. : 10/656897
DATED : January 15, 2008
INVENTOR(S) : Joel W. Schwartz et al.

It is certified that error appears in the above-identified patent and that said Letters Patent is hereby corrected as shown below:

In column 1, lines 8-11, delete
"The government owns rights in the present invention pursuant to grant numbers NS-34075, NS-33373 and DA016338 from the National Institutes of Health." and insert --This invention was made with government support under grant numbers NS-34075, NS-33373 and DA016338 awarded by the National Institutes of Health. The government has certain rights in the invention.-- therefor.

Signed and Sealed this

Twenty-first Day of April, 2009

JOHN DOLL
*Acting Director of the United States Patent and Trademark Office*